(12) United States Patent
Suzuki et al.

(10) Patent No.: US 7,338,721 B2
(45) Date of Patent: Mar. 4, 2008

(54) CONDENSED POLYCYCLIC COMPOUND AND ORGANIC LIGHT-EMITTING DEVICE USING THE SAME

(75) Inventors: Koichi Suzuki, Yokohama (JP); Tatsundo Kawai, Hadano (JP); Akihiro Senoo, Kawasaki (JP); Naoki Yamada, Inagi (JP); Akihito Saitoh, Yokohama (JP); Maki Okajima, Tachikawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 437 days.

(21) Appl. No.: 10/522,947

(22) PCT Filed: Aug. 26, 2003

(86) PCT No.: PCT/JP03/10783

§ 371 (c)(1),
(2), (4) Date: Feb. 2, 2005

(87) PCT Pub. No.: WO2004/020371

PCT Pub. Date: Mar. 11, 2004

(65) Prior Publication Data

US 2005/0236974 A1    Oct. 27, 2005

(30) Foreign Application Priority Data

Aug. 27, 2002  (JP)  ............... 2002-246600
Aug. 11, 2003  (JP)  ............... 2003-291191

(51) Int. Cl.
*H01L 51/54*   (2006.01)
*C09K 11/06*   (2006.01)
*C07C 13/567*  (2006.01)

(52) U.S. Cl. .............. 428/690; 428/917; 313/504; 313/506; 257/40; 257/E51.049; 585/26; 585/27

(58) Field of Classification Search ............ 585/26, 585/27
See application file for complete search history.

(56) References Cited

U.S. PATENT DOCUMENTS

| | | | |
|---|---|---|---|
| 3,250,780 A | 5/1966 | Rai et al. ................. 260/307 |
| 4,539,507 A | 9/1985 | VanSlyke et al. ........ 313/504 |
| 4,720,432 A | 1/1988 | VanSlyke et al. ........ 428/457 |
| 4,885,211 A | 12/1989 | Tang et al. ............... 428/457 |
| 5,130,603 A | 7/1992 | Tokailin et al. .......... 313/504 |
| 5,151,629 A | 9/1992 | VanSlyke ................. 313/504 |
| 5,247,190 A | 9/1993 | Friend et al. ............. 257/40 |
| 5,317,169 A | 5/1994 | Nakano et al. ........... 257/40 |
| 5,382,477 A | 1/1995 | Saito et al. ............... 428/690 |
| 5,409,783 A | 4/1995 | Tang et al. ............... 428/690 |
| 5,514,878 A | 5/1996 | Holmes et al. ........... 257/40 |
| 5,672,678 A | 9/1997 | Holmes et al. ........... 528/373 |
| 6,093,864 A | 7/2000 | Tokailin et al. .......... 585/25 |
| 6,203,933 B1 | 3/2001 | Nakaya et al. ........... 428/690 |
| 6,387,547 B1 | 5/2002 | Fujita et al. .............. 428/690 |
| 6,399,223 B1 | 6/2002 | Fujita et al. .............. 428/690 |
| 6,515,182 B2 * | 2/2003 | Hosokawa et al. ........ 564/427 |
| 6,652,997 B2 | 11/2003 | Suzuki et al. ............ 428/690 |
| 6,743,948 B1 * | 6/2004 | Hosokawa et al. ........ 564/426 |
| 2002/0177009 A1 | 11/2002 | Suzuki et al. ............ 428/690 |
| 2003/0039858 A1 * | 2/2003 | Igarashi et al. ........... 428/690 |
| 2004/0263067 A1 | 12/2004 | Saitoh et al. ............. 313/504 |
| 2005/0099115 A1 | 5/2005 | Saitoh et al. ............. 313/504 |

FOREIGN PATENT DOCUMENTS

| | | |
|---|---|---|
| JP | 04-068076 | 3/1992 |
| JP | 4-68076 | 3/1992 |
| JP | 05-032966 | 2/1993 |
| JP | 05-202356 | 8/1993 |
| JP | 05-247460 | 9/1993 |
| JP | 06-228552 | 8/1994 |
| JP | 07-109454 | 4/1995 |
| JP | 09-202878 | 8/1997 |
| JP | 09-227576 | 9/1997 |
| JP | 09-241629 | 9/1997 |
| JP | 2000-268964 | 9/2000 |
| JP | 2003-109764 | 4/2003 |
| WO | WO 03/007658 A2 | 1/2003 |

OTHER PUBLICATIONS

Machine Translation, JP 2003-109764, Suzuki et al.*

(Continued)

*Primary Examiner*—Terrel Morris
*Assistant Examiner*—Brett A. Crouse
(74) *Attorney, Agent, or Firm*—Fitzpatrick, Cella, Harper & Scinto

(57) ABSTRACT

A new condensed polycyclic compound represented by general formula [I]:

[I]

wherein $R_1$ is hydrogen, halogen, cyano, a substituted amino or a group selected from the group consisting of alkyl, aralkyl, aryl, heterocyclic, each having no substituent or a substituent; and $Ar_1$ to $Ar_5$ are the same or different and are each independently a condensed polycyclic aromatic group or a condensed polycyclic heterocyclic group, each having no substituent or a substituent is used for an organic light-emitting device that is extremely efficient in a light output with high luminance and is extremely durable.

10 Claims, 3 Drawing Sheets

OTHER PUBLICATIONS

Yamamoto et al., "A Novel Type of . . . C-CCoupling", Bull. Pf Chem., Soc. Jpn.; 51, (7) 2091-2097 (1978).

Ghosal, et al., "Formation of 1,3-Dienes . . . of Organotin Compound", J.g. Chem. 52, 4296-4298 (1987).

Tang et al., "Organic Electroluminescent Diodes", Appl. Phys. Lett., 51, (12) 913-915 (1987).

Burroughs et al., "Light-Emitting Diodes . . . Polymers", NATURE; vol. 347, pp. 539-541 (1990).

Miyaura et al., Palladium-Catalyzed Cross-Coupling . . . Compounds, Chem. Rev. vol. 7, No. 7, pp. 2447-2483 (1995).

Baldo et al., "Highly efficient . . . electroluminescent device", NATURE, 395, 151-154, 1998).

* cited by examiner

CONDENSED POLYCYCLIC COMPOUND AND ORGANIC LIGHT-EMITTING DEVICE USING THE SAME

TECHNICAL FIELD

The present invention relates to a new organic compound and an organic light-emitting device using the same.

BACKGROUND ART

An organic light-emitting device is a device in which a thin film containing a fluorescent organic compound or a phosphorescent organic compound is sandwiched between an anode and a cathode; an exciton of the fluorescent compound or the phosphorescent compound is produced by injecting an electron or a hole from each of the electrodes and the light radiated when the exciton returns to the ground state is utilized.

In a research by Eastman Kodak Company in 1987 (Appl. Phys. Lett. 51, 913 (1987)), there is reported a light emission of about 1,000 cd/m$^2$ at an applied voltage of about 10 V for a device of separated-function two-layered structure using ITO for anode and a magnesium-silver alloy for cathode, respectively, an aluminum-quinolinol complex as an electron-transporting material and a light-emitting material and a triphenylamine derivative as a hole transporting material. Related patents include U.S. Pat. No. 4,539,507; U.S. Pat. No. 4,720,432 and U.S. Pat. No. 4,885,211.

In addition, light-emission from ultraviolet to infrared is possible by changing the type of fluorescent organic compounds and researches of various compounds have been conducted actively recently. For example, they are described in U.S. Pat. Nos. 5,151,629; 5,409,783; 5,382,477; 5,130,603; 6,093,864; 5,227,252; Japanese Patent Application Laid-Open No. H05-202356; Japanese Patent Application Laid-Open No. H09-202878 and Japanese Patent Application Laid-Open No. H09-227576.

In recent years, there have been a number of studies in which phosphorescent compounds are used as a light-emitting material and the energy in a triplet state is used for an EL emission. A group of Princeton University has reported that an organic light-emitting device using an iridium complex as a light-emitting material exhibits a high light-emitting efficiency (Nature 395, 151 (1998)).

Moreover, a group of Cambridge University has reported (Nature 347, 539 (1990)) an organic light-emitting device using a conjugated polymer other than the organic light-emitting device using monomeric materials as described above. In this report the light-emission in a monolayer is confirmed by forming a film of polyphenylenevinylene (PPV) in a coating system.

The related patents on organic light-emitting devices using conjugated polymers include U.S. Pat. Nos. 5,247,190; 5,514,878; 5,672,678; 5,317,169; 5,726,457 and Japanese Patent Application Laid-Open No. H05-247460.

Thus, recent progress in organic light-emitting devices is remarkable, and possibilities for a wide range of applications are indicated since it is characterized in that a thin and light-weight light-emitting device having high luminance at a low applied-voltage, diversity of light-emitting wavelength and high-speed response can be prepared.

However, a higher-luminance light output or high conversion efficiency is required under present circumstances. In addition, there are numbers of problems in terms of durability such as the variation with time during use for a long period of time and the deterioration due to an atmospheric gas containing oxygen or humidity. Moreover, the light-emission of blue, green and red having a good color purity is required for applications such as a full-color display, but these issues are not sufficiently satisfied.

Aromatic compounds and condensed polycyclic aromatic compounds have been studied in great numbers as fluorescent organic compounds to be used for an electron-transporting layer or a light-emitting layer. These include, for example, Japanese Patent Application Laid-Open No. H04-68076; Japanese Patent Application Laid-Open No. H05-32966; Japanese Patent Application Laid-Open No. H06-228552; Japanese Patent Application Laid-Open No. H06-240244; Japanese Patent Application Laid-Open No. H07-109454; U.S. Pat. No. 6,203,933; Japanese Patent Application Laid-Open No. H09-241629; U.S. Pat. No. 6,387,547; U.S. Pat. No. 6,399,223 and Japanese Patent Application Laid-Open No. 2000-268964. However, nothing that sufficiently satisfies light-emission luminance and durability has been obtained so far.

DISCLOSURE OF THE INVENTION

It is an object of the present invention to provide a new condensed polycyclic compound.

It is a further object of the present invention to provide an organic light-emitting device having a light output with an extremely high efficiency and high luminance using a specific condensed polycyclic compound.

It is a further object of the present invention to provide an extremely durable organic light-emitting device.

It is a further object of the present invention to provide an organic light-emitting device that is easily produced and can be prepared at a relatively low cost.

Specifically, the present invention provides a condensed polycyclic compound represented by general formula [I] or [II]:

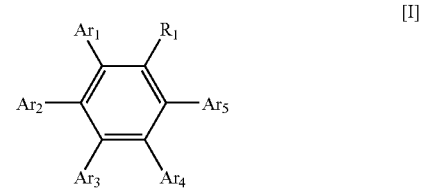

[I]

wherein $R_1$ is hydrogen, halogen, cyano, a substituted amino or a group selected from the group consisting of alkyl, aralkyl, aryl, heterocyclic, each having no substituent or a substituent; and $Ar_1$ to $Ar_5$ are the same or different and are each independently a condensed polycyclic aromatic group or a condensed polycyclic heterocyclic group, each having no substituent or a substituent; and

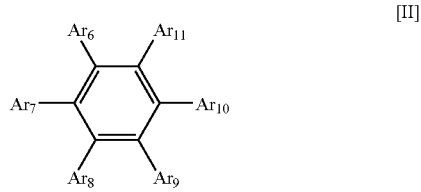

[II]

wherein $Ar_6$ to $Ar_{11}$ are the same or different and are each independently a group selected from the group consisting of condensed polycyclic aromatic groups and condensed polycyclic heterocyclic groups, each having no substituent or a substituent.

The present invention further provides an organic light-emitting device comprising a pair of electrodes consisting of an anode and a cathode and organic compound-containing layers sandwiched between the pair of electrodes, wherein at least one layer of the organic compound-containing layers contains at least one compound selected from the group consisting of the condensed polycyclic compounds.

BEST MODE FOR CARRYING OUT THE INVENTION

Figure 1:
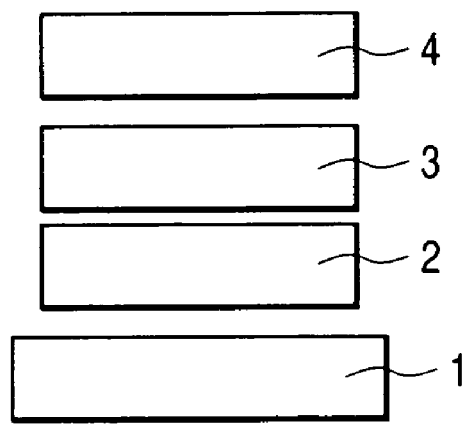
FIG. 1 is a sectional view illustrating one example of the organic light-emitting device according to the present invention.

The present invention will now be described in detail.

The condensed polycyclic compounds of the present invention will be first described.

The condensed polycyclic compounds of the present invention are represented by the above general formula [I] or [II].

Herein, at least one of $Ar_1$ to $Ar_5$ or at least one of $Ar_6$ to $Ar_{11}$ is preferably a condensed polycyclic aromatic group represented by general formula [III]:

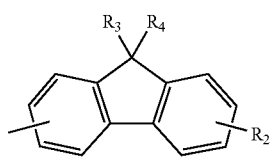

wherein $R_2$ is hydrogen, halogen, cyano, a substituted amino or a group selected from the group consisting of alkyl, aralkyl, aryl and heterocyclic, each having no substituent or a substituent; and $R_3$ and $R_4$ are the same or different and are each independently hydrogen or a group selected from the group consisting of alkyl, aralkyl, aryl and heterocyclic, each having no substituent or a substituent.

Further, the condensed polycyclic compounds of the present invention are more preferably represented by any of general formulas.

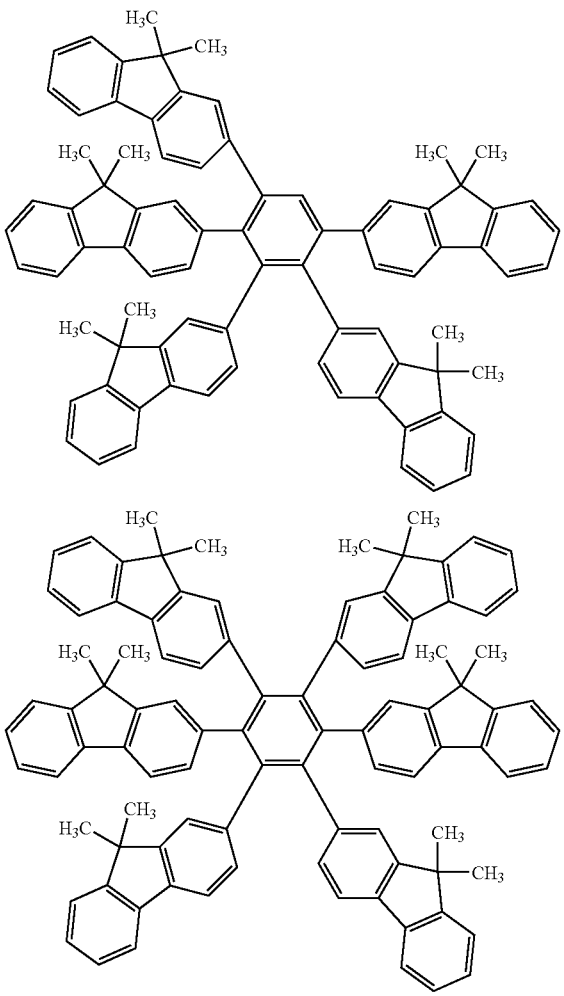

Furthermore, at least one of $Ar_1$ to $Ar_5$ or at least one of $Ar_6$ to $Ar_{11}$ preferably denotes a condensed polycyclic aromatic group represented by any of general formulas [IV] to [VII]:

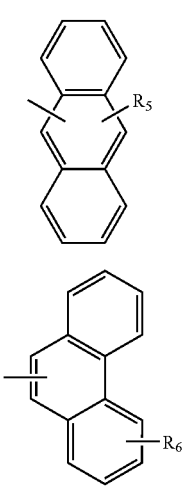

-continued

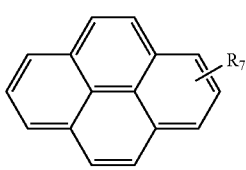  [VI]

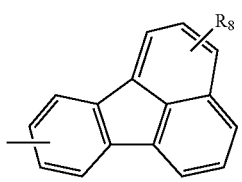  [VII]

wherein $R_5$ to $R_8$ are hydrogen, halogen, cyano, a substituted amino or a group selected from the group consisting of alkyl, aralkyl, aryl and heterocyclic, each having no substituent or a substituent.

Specific examples for the substituent groups in the above general formulas [I] to [VII] are shown below.

The alkyl group includes methyl, ethyl, n-propyl, iso-propyl, n-butyl, ter-butyl, octyl or the like.

The aralkyl group includes benzyl, phenethyl or the like.

The aryl group includes phenyl, biphenyl, terphenyl or the like.

The heterocyclic group includes thienyl, pyrolyl, pyridyl, oxazolyl, oxadiazolyl, thiazolyl, thidiazolyl, terthienyl or the like.

The substituted amino group includes dimethylamino, diehtylamino, dibenzylamino, diphenylamino, ditolylamino, dianisolylamino or the like.

The halogen atom includes fluorine, chlorine, bromine, iodine or the like.

The condensed polycyclic aromatic group includes fluorenyl, naphthyl, fluoranthenyl, anthryl, phenathryl, pyrenyl, tetracenyl, pentacenyl or the like.

The condensed polycyclic heterocyclic group includes quinolyl, diazafluorenyl, acrydinyl, phenanthrolyl or the like.

The substituent groups that the above substituent groups may have include alkyl groups such as methyl, ethyl and propyl; aralkyl groups such as benzyl and phenethyl; aryl groups such as phenyl and biphenyl; heterocyclic groups such as thienyl, pyrolyl and pyridyl; amino groups such as dimethylamino, diethylamino, dibenzylamino, diphenylamino, ditolylamino and dianisolylamino; alkoxyl groups such as methoxyl, ethoxyl, propoxyl and phenoxyl; cyano group and halogen atoms such as fluorine, chlorine, bromine and iodine.

The followings are typical examples of the condensed polycyclic compounds of the present invention, but the present invention is not limited thereto:

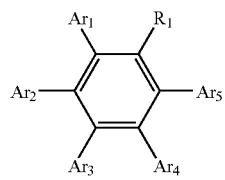  [I]

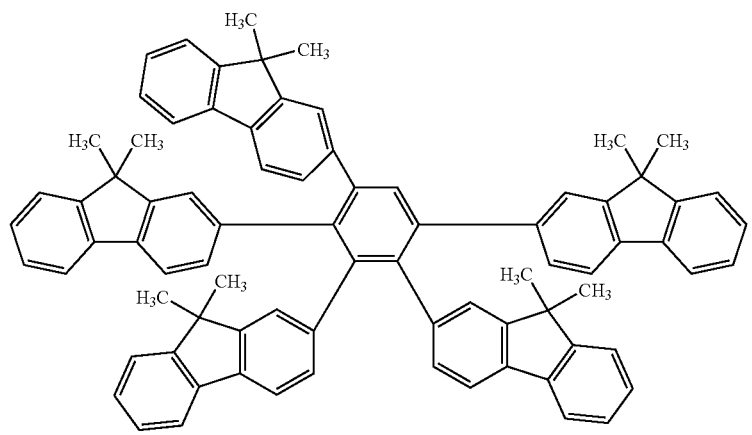

1

-continued
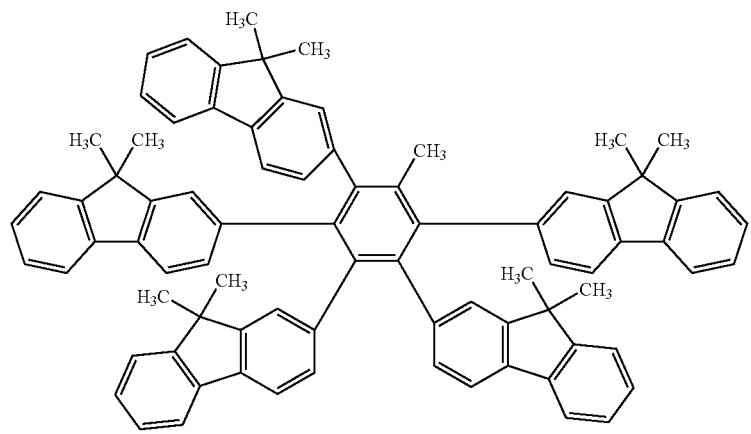
2
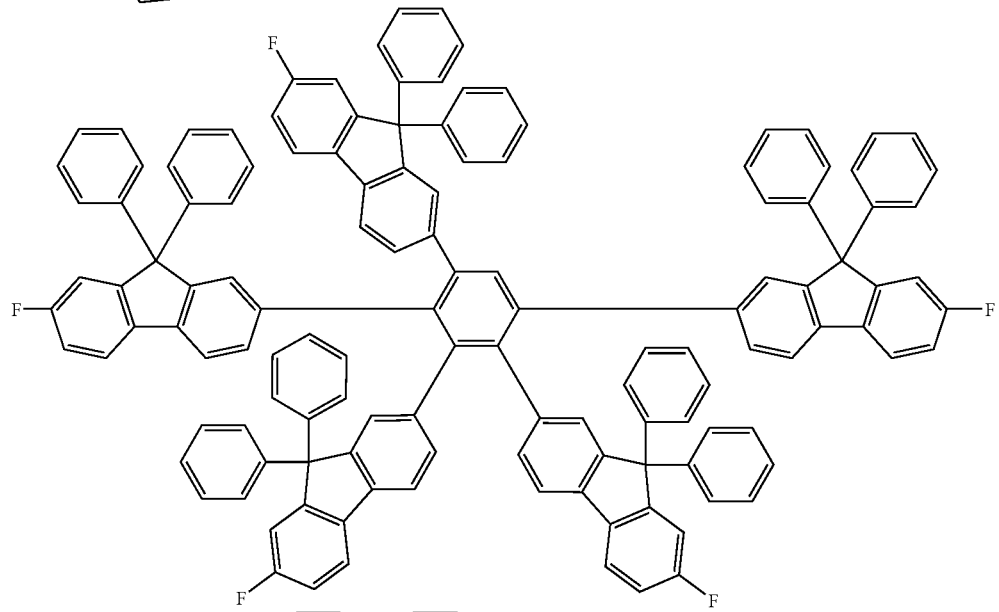
3
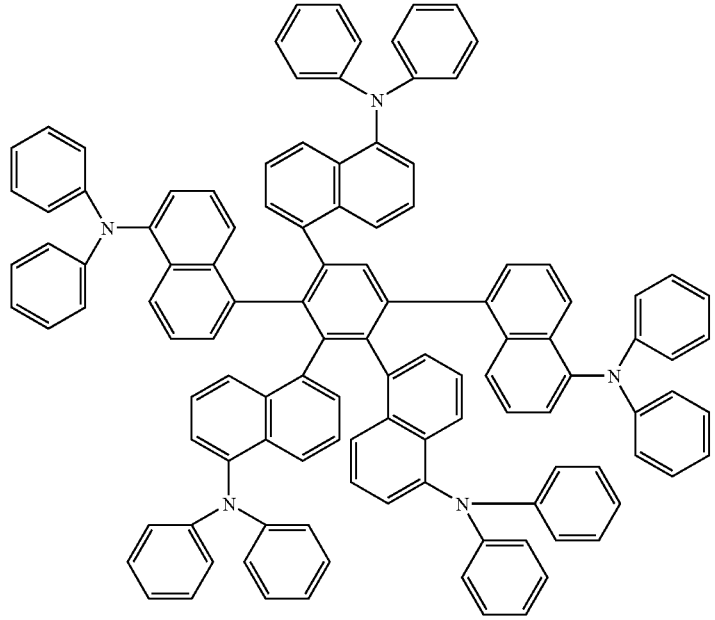
4

-continued
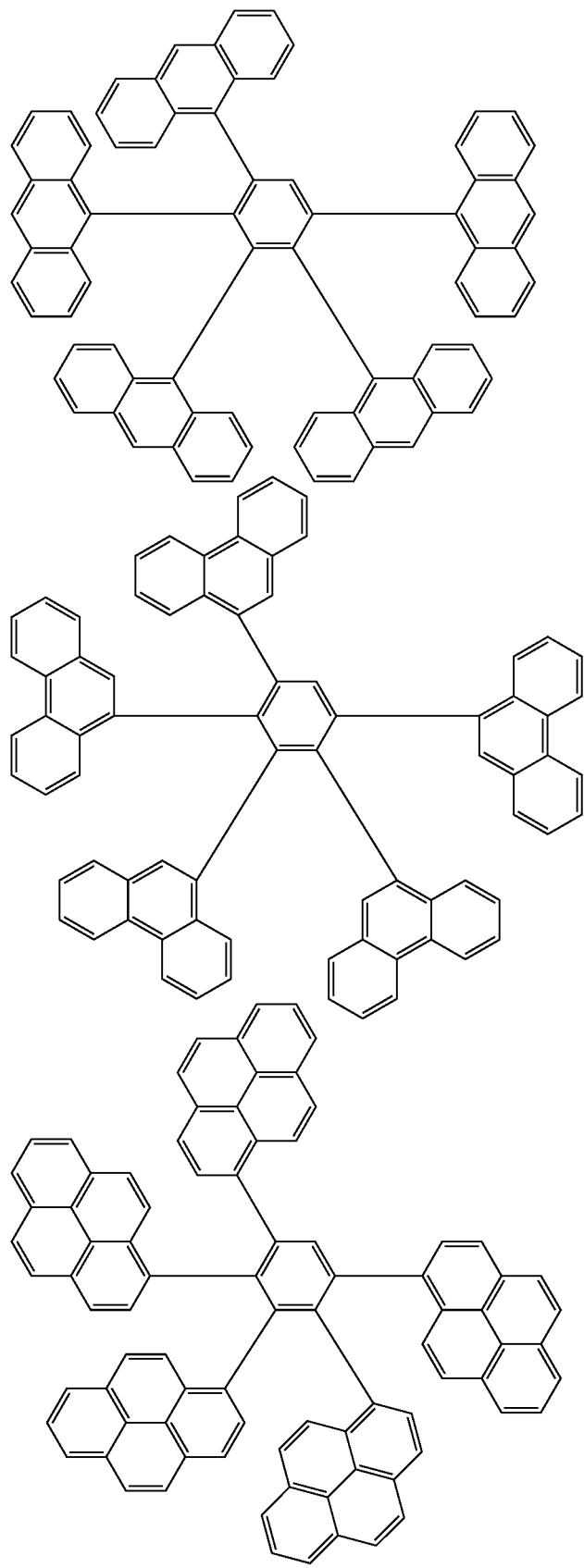
5
6
7

-continued
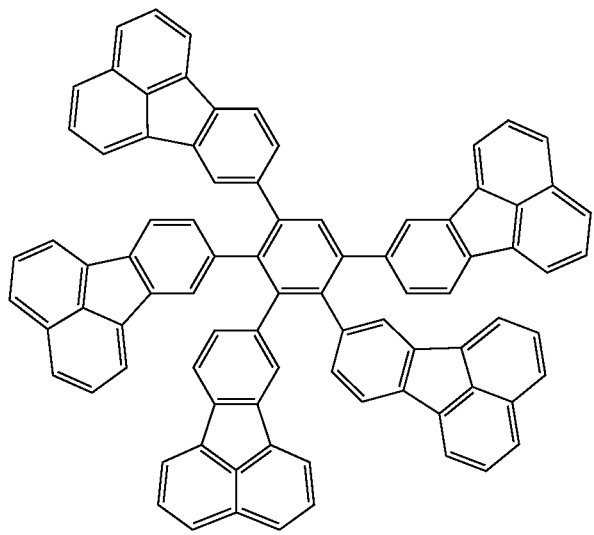
8
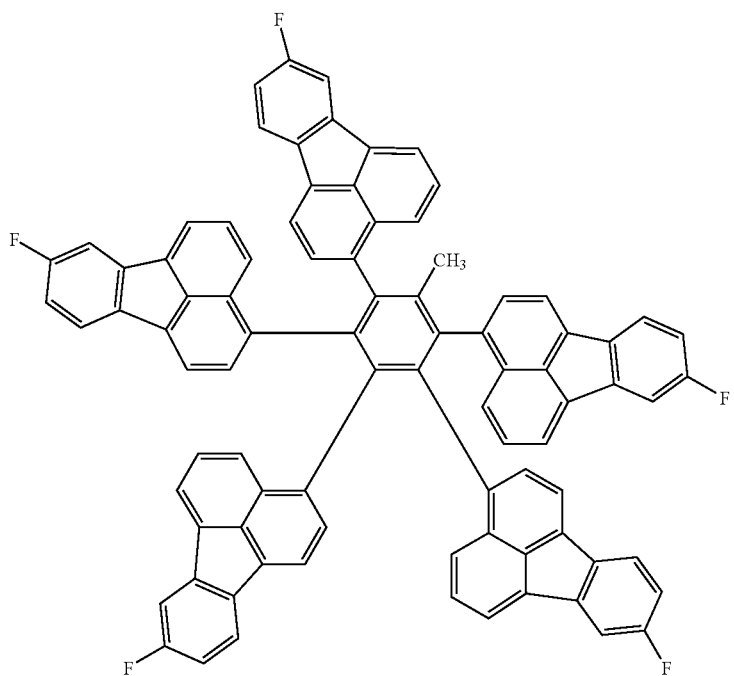
9

-continued
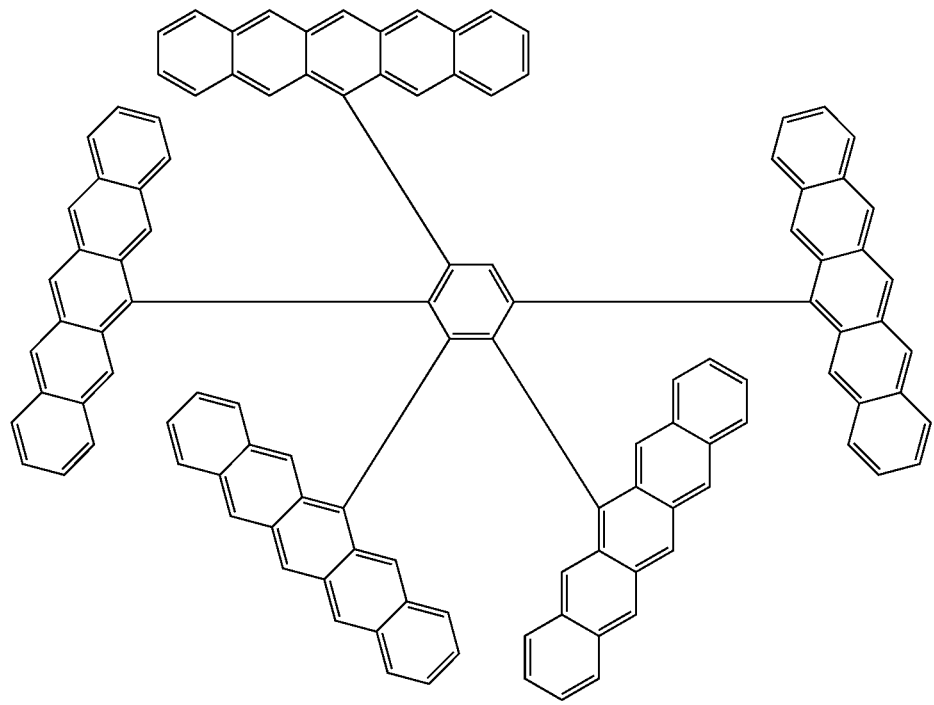
10
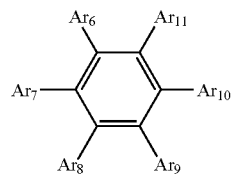
[II]
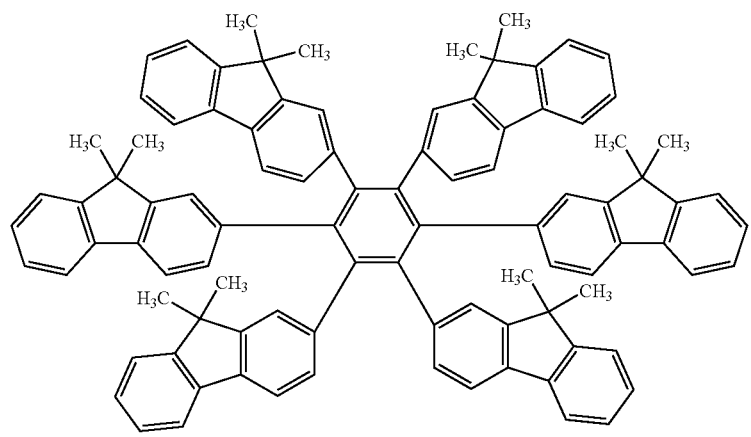
11

-continued
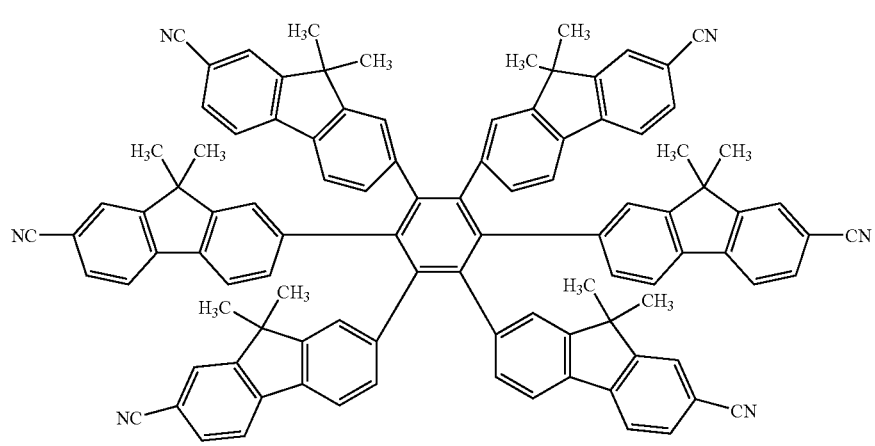
12
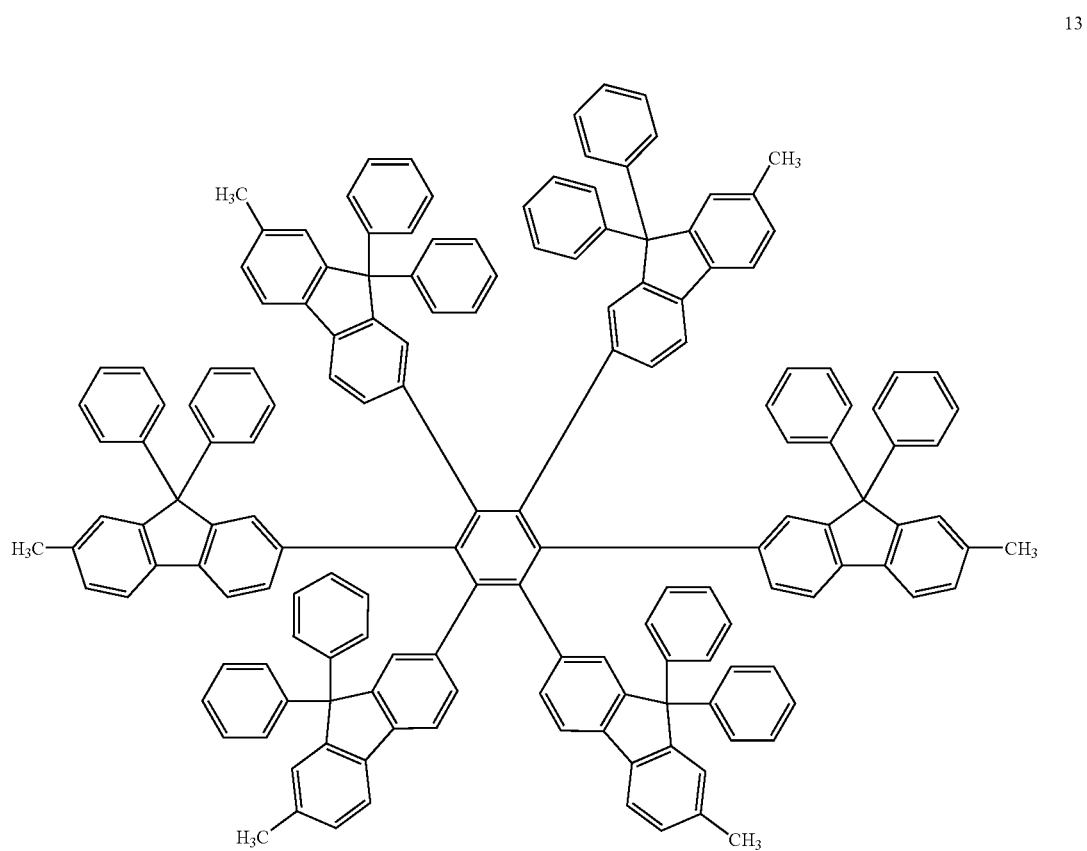
13

-continued
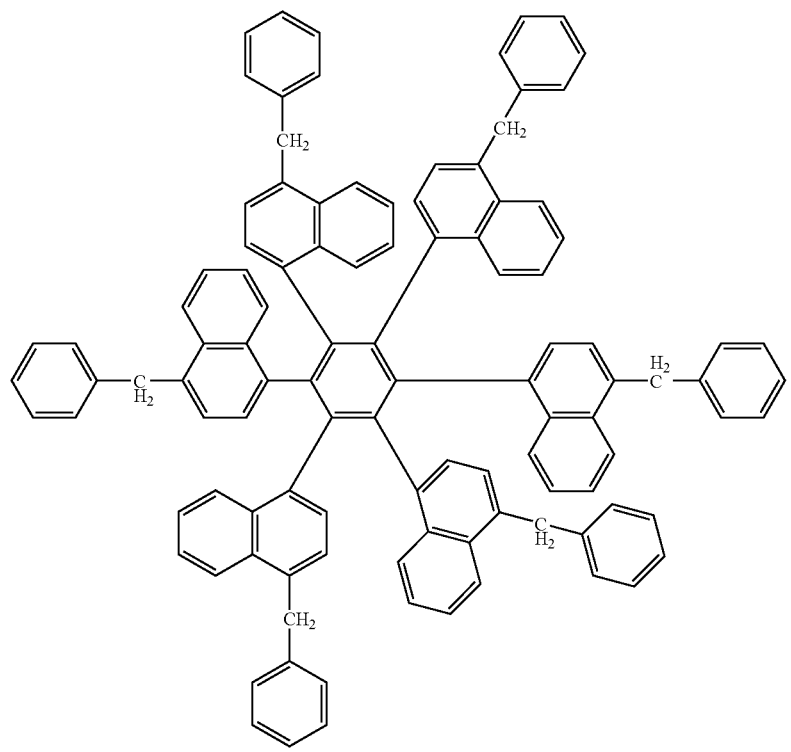
14
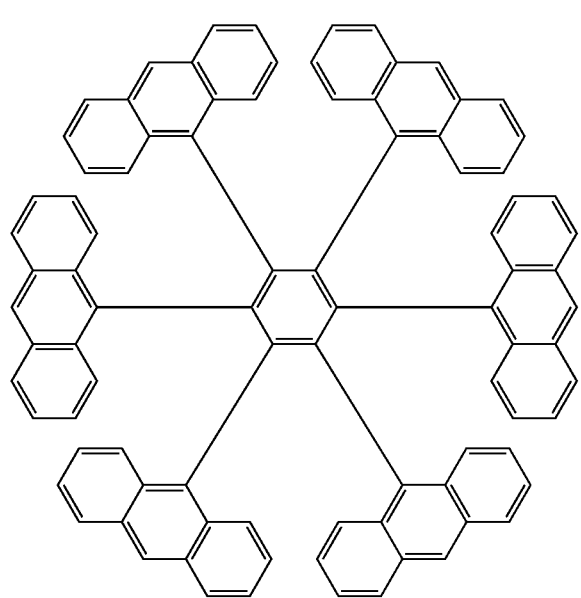
15

-continued
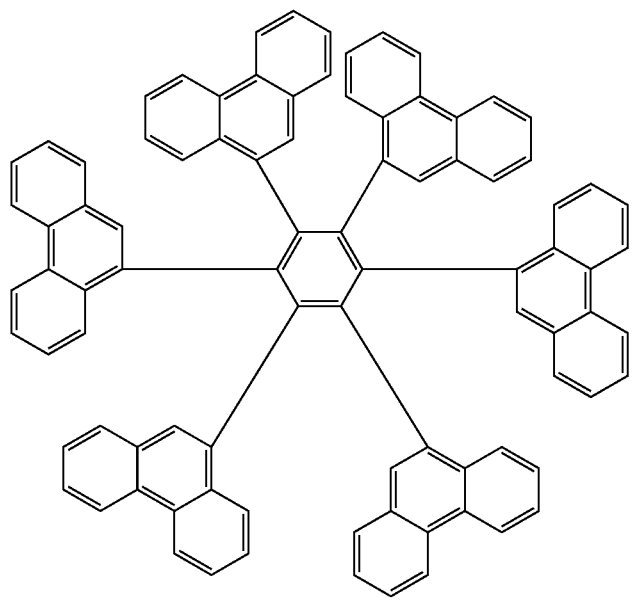
16
17

-continued
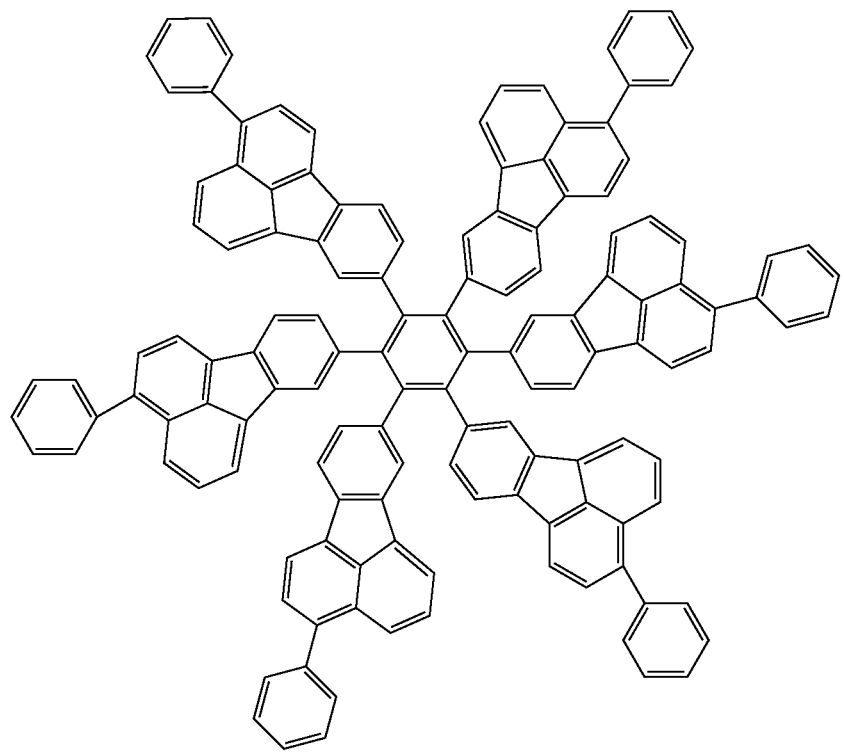
18
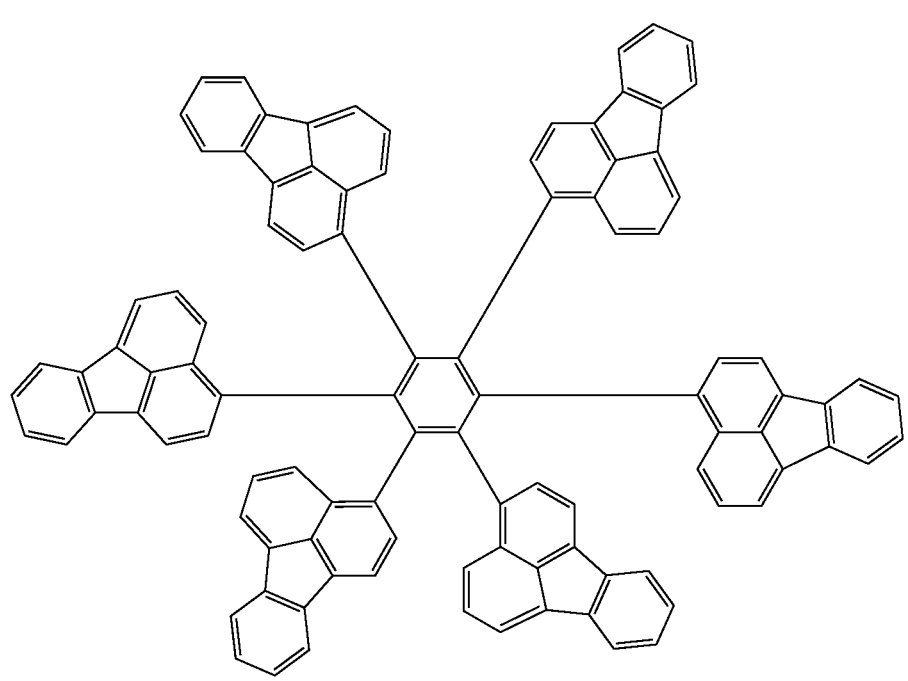
19

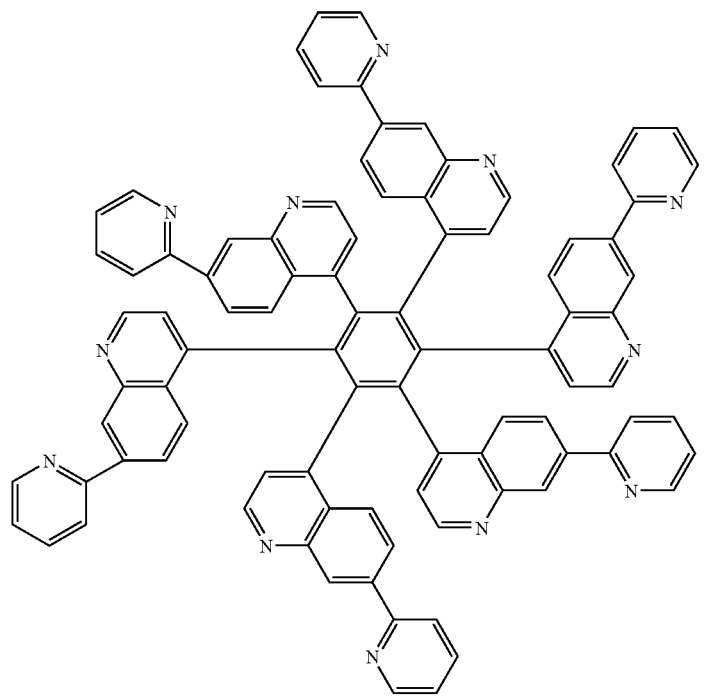
20
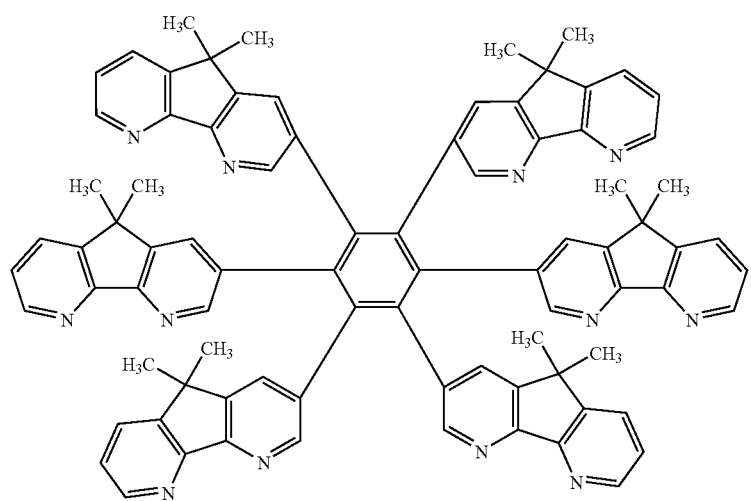
21

-continued

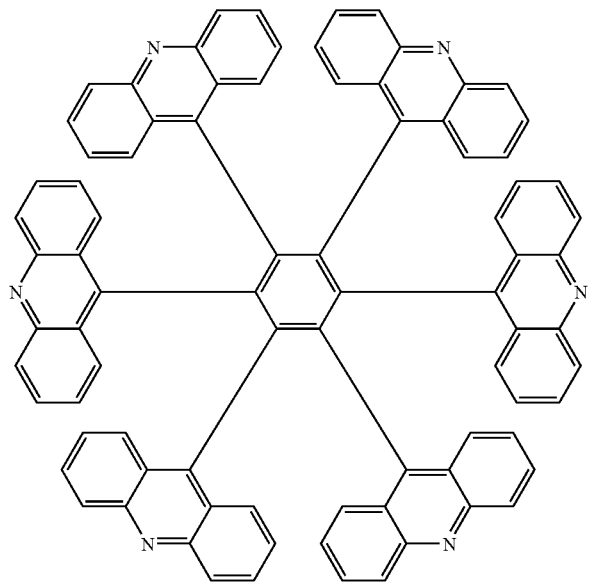

The condensed polycyclic compounds of the present invention can be synthesized by generally known methods, and can be obtained by synthesis methods such as, for example, Suzuki coupling method using a palladium catalyst (e.g., Chem. Rev. 1995, 95, 2457-2483); Yamamoto method using a nickel catalyst (e.g., Bull. Chem. Soc. Jpn. 51, 2091, 1978) and a synthesizing method using aryltin compounds (e.g., J. Org. Chem., 52, 4296, 1987).

The condensed polycyclic compounds of the present invention are excellent in an electron-transporting property, a light-emitting property and durability compared with conventional compounds, and are useful for an organic compound-containing layer, in particular, an electron-transporting layer and a light-emitting layer in an organic light-emitting device. In addition, the layer formed by a vacuum deposition process or a solution coating process hardly causes crystallization or the like and is excellent in the stability with time.

The organic light-emitting device of the present invention will now be described in detail.

The organic light-emitting device of the present invention at least comprises a pair of electrodes consisting of an anode and a cathode and one or a plurality of organic compound-containing layers sandwiched between the pair of electrodes, wherein at least one layer of the above-described organic compound-containing layers contains at least one compound selected from the group consisting of the condensed polycyclic compounds represented by the above general formula [I] or general formula [II].

In the organic light-emitting device of the present invention, at least the electron transporting layer or the light-emitting layer among the organic compound-containing layers preferably contains at least one selected from the group consisting of the above-described condensed polycyclic compounds.

In the organic light-emitting device of the present invention, the condensed polycyclic compounds represented by the above general formula [I] or general formula [II] are formed between the anode and the cathode by a vacuum deposition process or a solution coating process. The organic layer is preferably formed in a thin film having a thickness of less than 10 μm, preferably 0.5 μm or less, more preferably from 0.01 to 0.5 μm.

The organic light-emitting device of the present invention comprises a preferred embodiment that at least the light-emitting layer of the organic compound-containing layers contains at least one selected from the group consisting of the condensed polycyclic compounds and a fluorene compound represented by general formula [VIII] or [IX]:

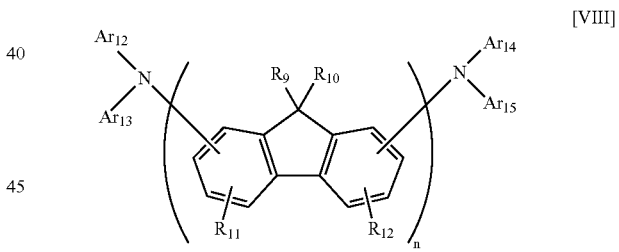

[VIII]

wherein $R_9$ and $R_{10}$ are the same or different and are each independently hydrogen or a group selected from the group consisting of alkyl, aralkyl, aryl and heterocyclic, each having no substituent or a substituent; any pair of $R_9$ combined to their respective fluorene structures are the same or different to each other; any pair of $R_{10}$ combined to their respective fluorene structures are the same or different to each other; $R_{11}$ and $R_{12}$ are the same or different and are each independently hydrogen, halogen, cyano or a group selected from the group consisting of alkyl, aralkyl, aryl and heterocyclic, each having no substituent or a substituent; any pair of $R_{11}$ combined to their respective fluorene structures are the same or different to each other; any pair of $R_{12}$ combined to their respective fluorene structures are the same or different to each other; $Ar_{12}$, $Ar_{13}$, $Ar_{14}$ and $Ar_{15}$ are the same or different and are each independently a group selected from the group consisting of aromatic, heterocyclic, condensed polycyclic aromatic and condensed polycyclic heterocyclic, each having no substituent or a substituent, and $Ar_{12}$ and $Ar_{14}$ can be bonded to $Ar_{13}$ and $Ar_{15}$ respectively to form a ring; and n is an integer from 1 to 10, and

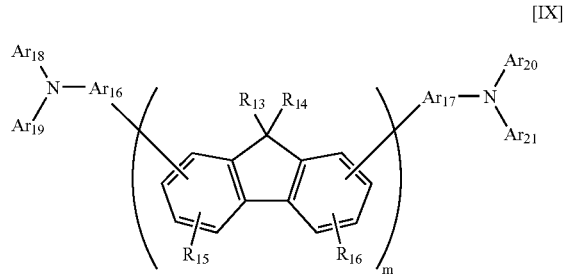

[IX]

wherein $R_{13}$ and $R_{14}$ are the same or different and are each independently hydrogen or a group selected from the group consisting of alkyl, aralkyl, aryl and heterocyclic, each having no substituent or a substituent; any pair of $R_{13}$ combined to their respective fluorene structures are the same or different to each other; any pair of $R_{14}$ combined to their respective fluorene structures are the same or different to each other; $R_{15}$ and $R_{16}$ are the same or different and are each independently hydrogen, halogen, cyano or a group selected from the group consisting of alkyl, aralkyl, aryl and heterocyclic, each having no substituent or a substituent; any pair of $R_{15}$ combined to their respective fluorene structures are the same or different to each other; any pair of $R_{16}$ combined to their respective fluorene structures are the same or different to each other; $Ar_{16}$ and $Ar_{17}$ are the same or different and are each independently a divalent group selected from the group consisting of divalent aromatic and divalent heterocyclic, each having no substituent or a substituent; $Ar_{18}$, $Ar_{19}$, $Ar_{20}$ and $Ar_{21}$ are the same or different and are each independently a group selected from the group consisting of aromatic, heterocyclic, condensed polycyclic aromatic and condensed polycyclic heterocyclic, each having no substituent or a substituent, and $Ar_{18}$ and $Ar_{20}$ can be bonded to $Ar_{19}$ and $Ar_{21}$ respectively to form a ring; and m is an integer from 1 to 10.

Examples of the substituent groups in the general formulas [VIII] and [IX] are similar to those in the above general formulas [I] to [VII]. The followings are typical examples of the fluorene compounds represented by the general formula [VIII] or [IX], but the present invention is not limited thereto:

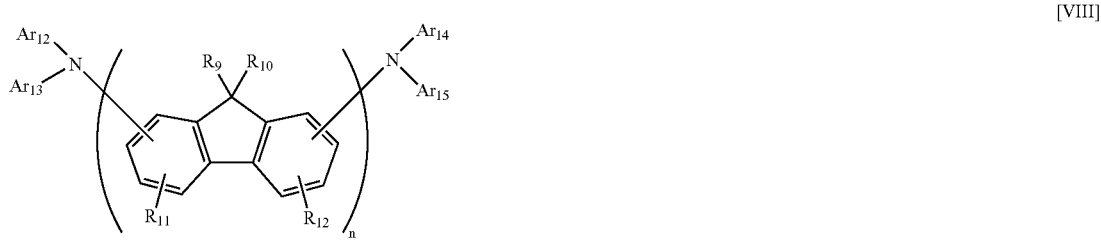

[VIII]

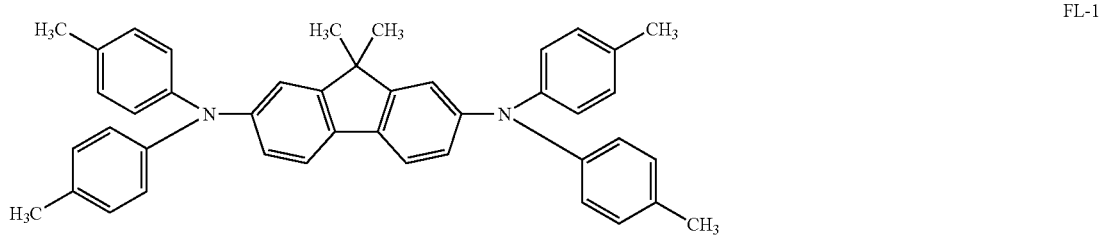

FL-1

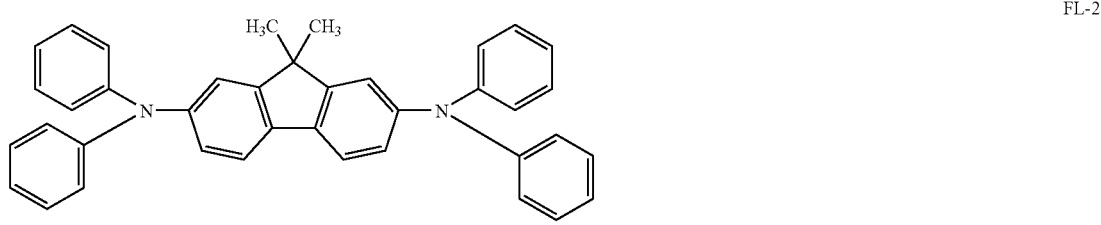

FL-2

-continued
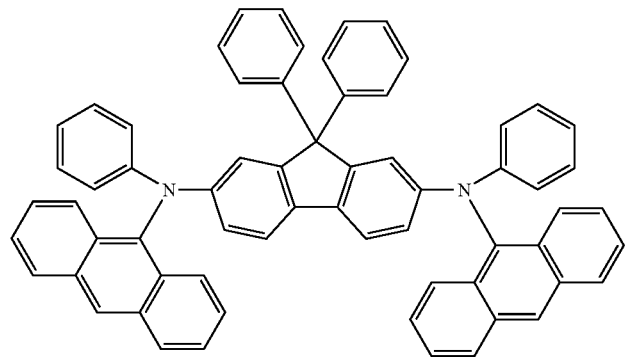
FL-3
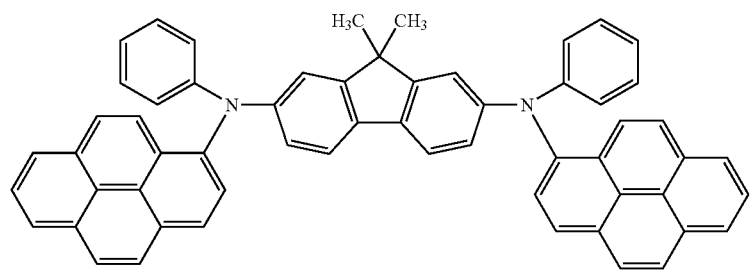
FL-4
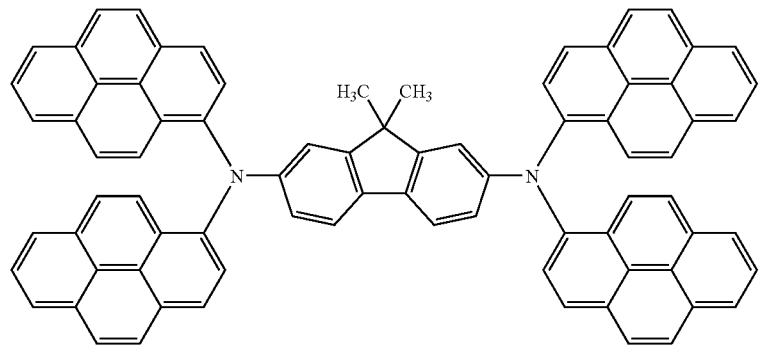
FL-5
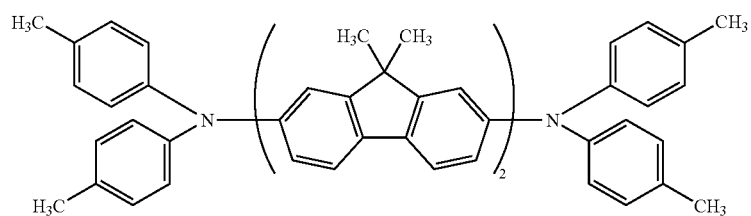
FL-6
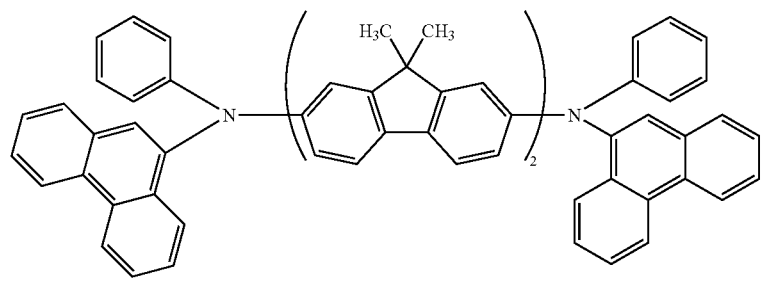
FL-7

FL-8
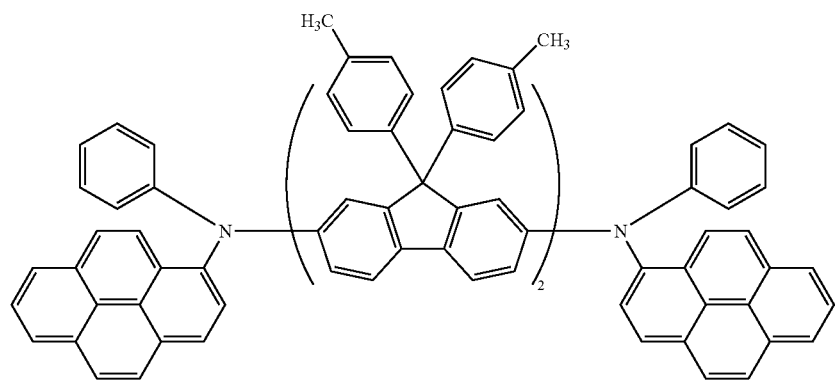
FL-9
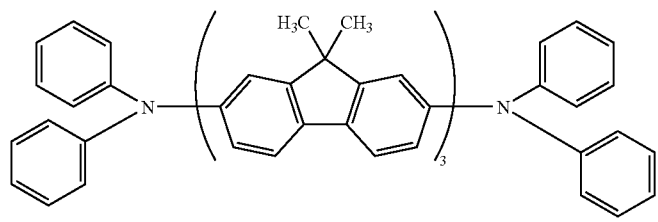
FL-10
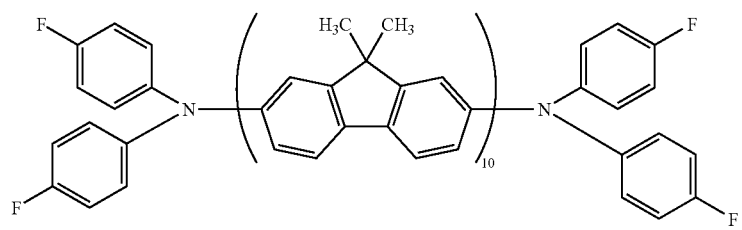
[IX]
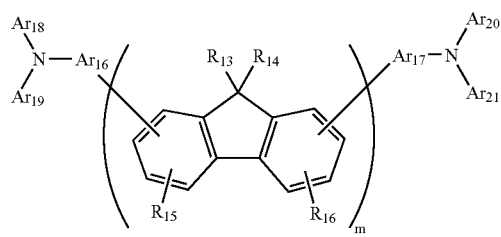
FL-11
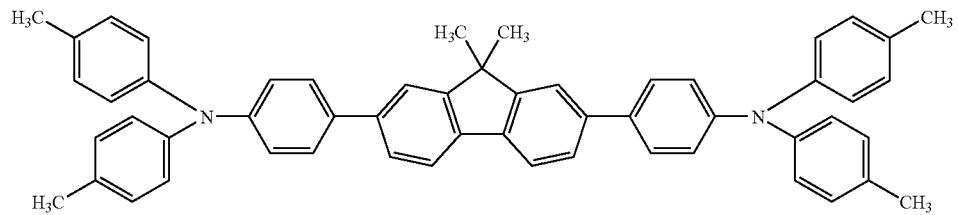
FL-12
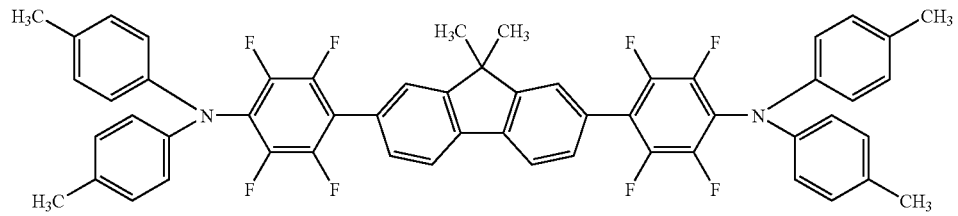

-continued
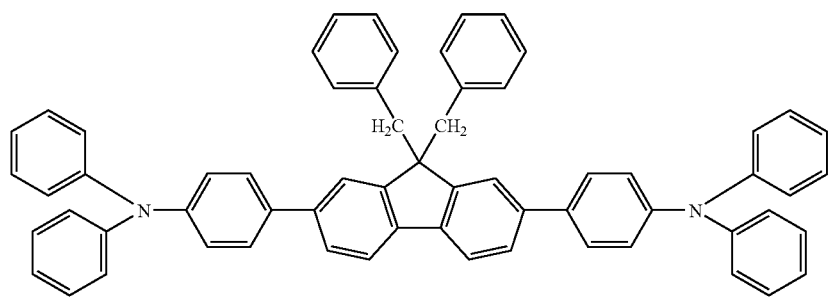
FL-13
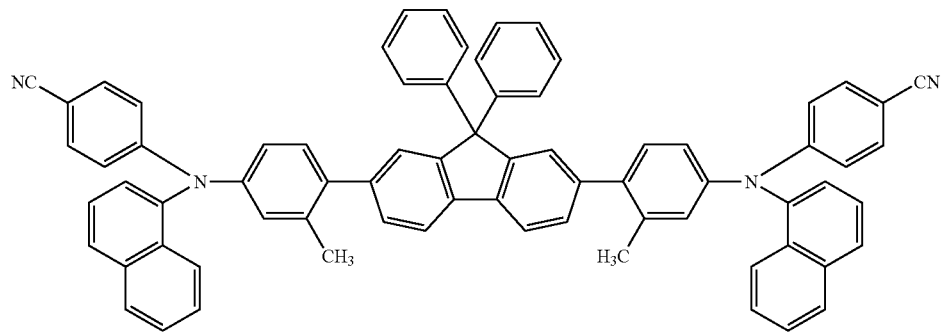
FL-14
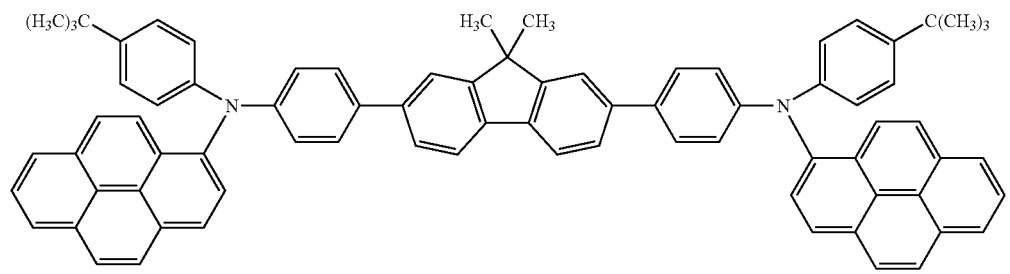
FL-15
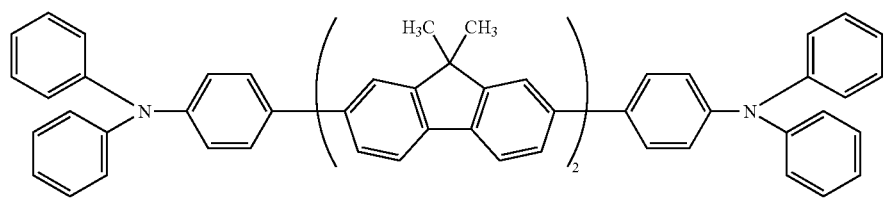
FL-16
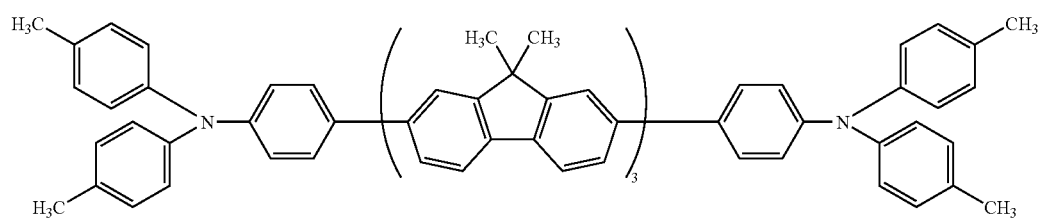
FL-17
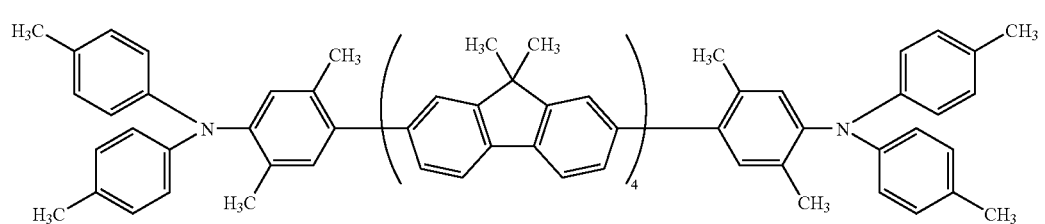
FL-18

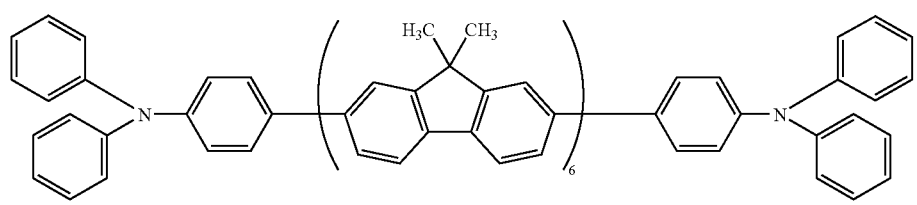

FL-19

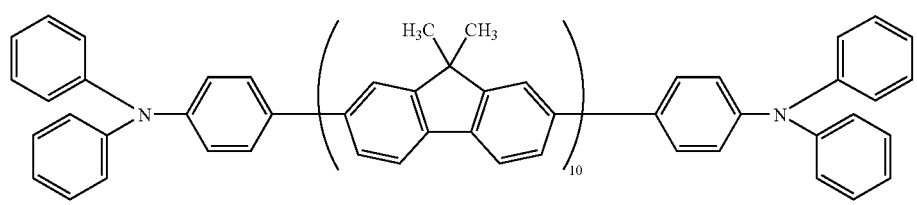

FL-20

FIGS. 1 to 6 illustrate preferred examples of the organic light-emitting devices of the present invention.

The example of FIG. 1 has the structure in which an anode 2, a light-emitting layer 3 and a cathode 4 are provided on a substrate 1 in this order. The light-emitting device herein used is useful when it has a hole-transporting capability, an electron-transporting capability and light-emitting performance singly within itself, or when compounds having respective characteristics are mixed for use.

Figure 2:
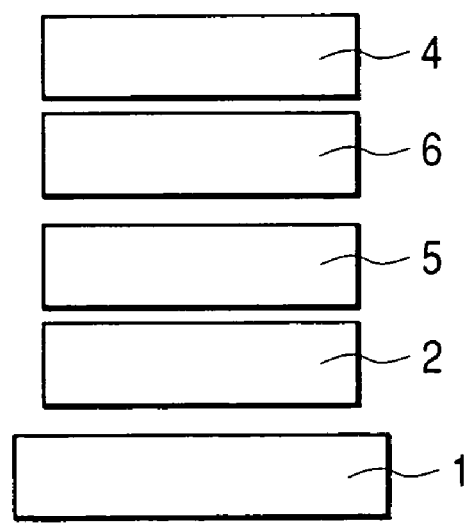
FIG. 2 is a sectional view illustrating another example of the organic light-emitting device according to the present invention.

The example of FIG. 2 has the structure in which an anode 2, a hole-transporting layer 5, an electron-transporting layer 6 and a cathode 4 are provided on a substrate 1 in this order. This example is useful when a material having a hole-transporting capability and/or an electron-transporting capability is used for respective layers as a light-emitting substance in combination with a mere hole-transporting substance or an electron-transporting substance having no light-emitting property. In this case, the light-emitting layer comprises the hole-transporting layer 5 or the electron-transporting layer 6.

Figure 3:
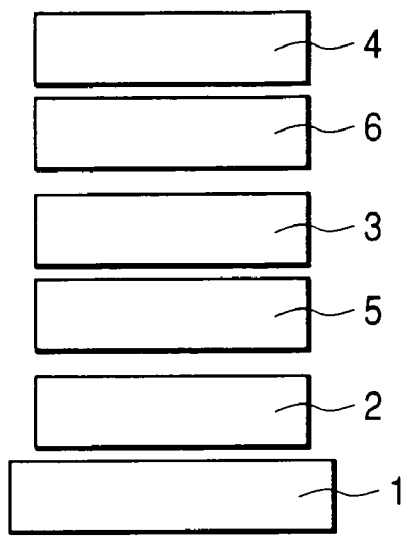
FIG. 3 is a sectional view illustrating another example of the organic light-emitting device according to the present invention.

The example of FIG. 3 has the structure in which an anode 2, a hole-transporting layer 5, a light-emitting layer 3, an electron-transporting layer 6 and a cathode 4 are provided on a substrate 1 in this order, a carrier-transporting function and a light-emitting function being separated. The separation of the light-emitting layer from the charge-transporting layer extremely increases the freedom of material selection since a compound having each property such as a hole-transporting property, an electron-transporting property or a light-emitting property can be used in a suitable combination. For example, various compounds having different light-emitting wavelengths can be used to allow diversification of the hue of light emission. Further, it is also possible to try to improve the efficiency of light emission by effectively confining each carrier or exciton in the central light-emitting layer 3.

Figure 4:
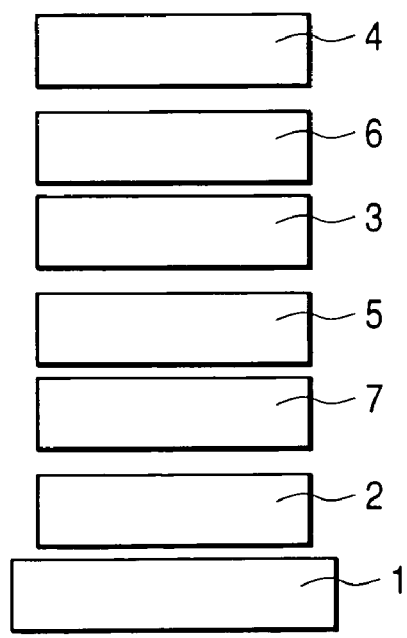
FIG. 4 is a sectional view illustrating another example of the organic light-emitting device according to the present invention.

The example of FIG. 4 has the structure in which a hole-injecting layer 7 is inserted between the anode 2 and the hole-transporting layer 5 in the form of FIG. 3, which is effective for improving adhesiveness of the anode 2 to the hole-transporting layer 5 or to improve a hole-injecting property, being effective to reduce voltage.

Figure 5:
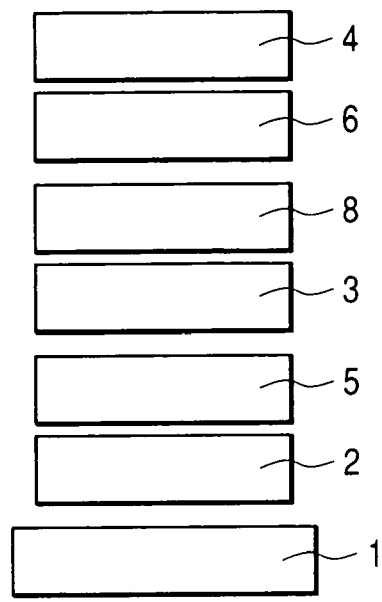
FIG. 5 is a sectional view illustrating another example of the organic light-emitting device according to the present invention.
Figure 6:
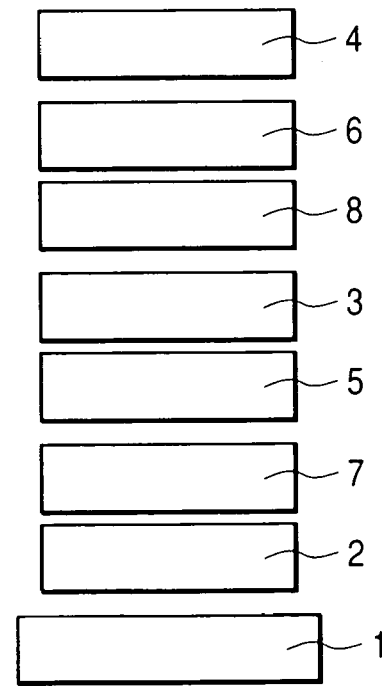
FIG. 6 is a sectional view illustrating another example of the organic light-emitting device according to the present invention.

Examples of FIGS. 5 and 6 have the structure in which a layer for blocking a hole or an exciton from passing through to the side of the cathode 4 (hole-blocking layer 8) is inserted between the light-emitting layer 3 and the electron-transporting layer 6 in the forms of FIGS. 3 and 4. The use of a compound having a very high ionization potential as the hole-blocking layer 8 is effective for improving the efficiency of light-emission.

FIGS. 1 to 6 are very basic device structures, and the structures of the organic light-emitting device using the compounds of the present invention are not limited to these. It is possible to take the structure of diversified layers, for example, to provide an insulating layer to the interface between the electrodes and the organic layers, to provide an adhesion layer or an interference layer or to compose a hole-transporting layer from two layers having different ionization potentials.

The condensed polycyclic compounds represented by the general formula [I] or the general formula [II] used in the present invention are excellent in an electron-transporting property, a light-emitting property and durability compared with conventional compounds, and can be used in any forms shown in FIGS. 1 to 6.

Although the present invention uses the condensed polycyclic compounds represented by the general formula [I] or the general formula [II] as constituent components for the electron-transporting layer or the light-emitting layer, already known hole-transporting compounds, light-emitting compounds or electron-transporting compounds can also be used together as necessary.

Examples of these compounds include the followings:
Hole-Transporting Compounds
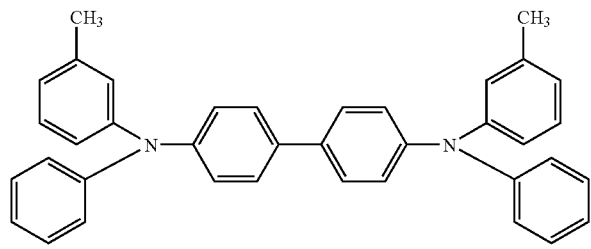
TPD
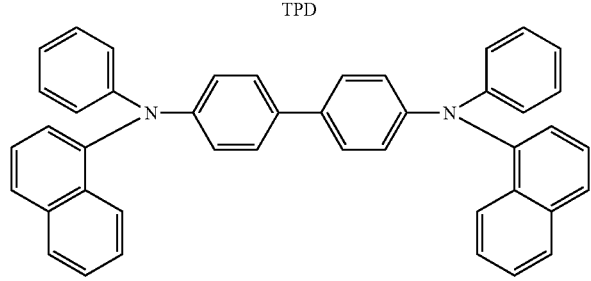
α-NPD
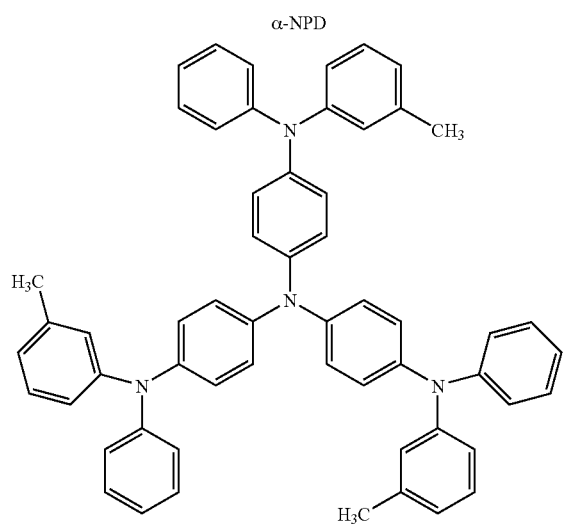
m-MTDATA
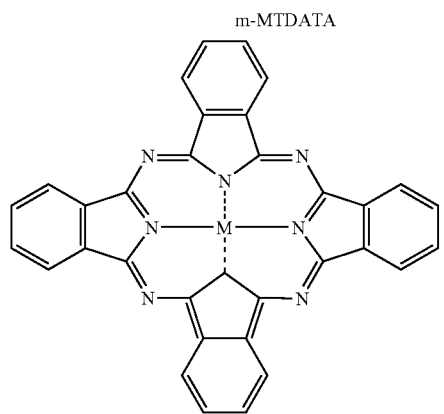
Pc-M
M: Cu, Mg, AlCl, TiO, SiCl$_2$, Zn, Sn,
MnCl, GaCl, etc -continued
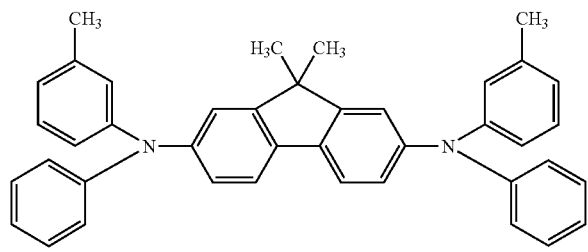
DTDPFL
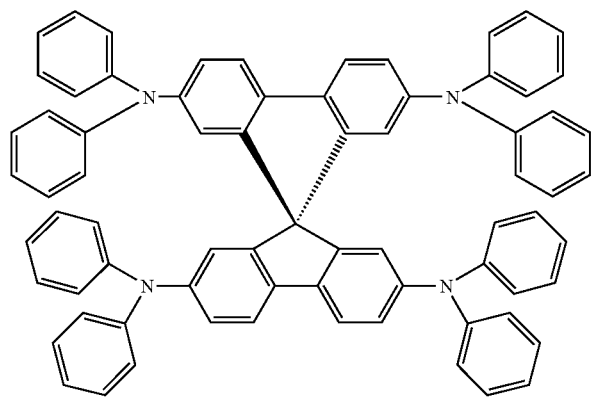
spiro-TPD
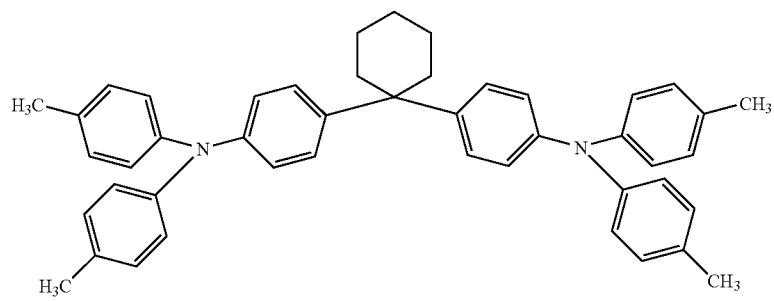
TPAC
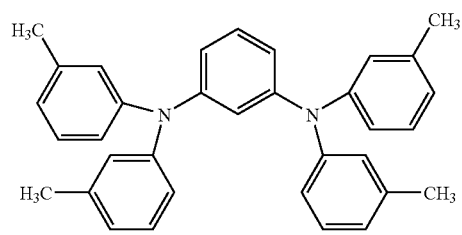
PDA Electron-Transporting Light-Emitting Materials
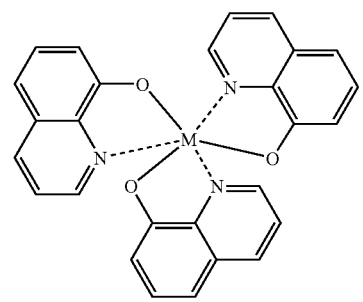
M: Al, Ga
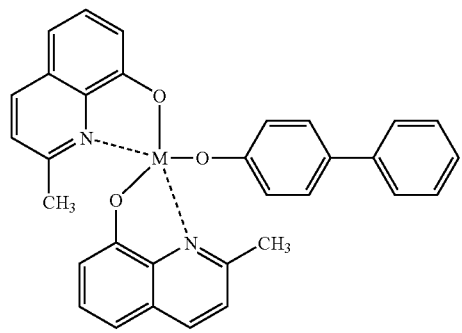
M: Al, Ga
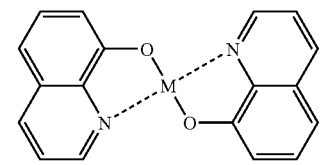
M: Zn, Mg, Be
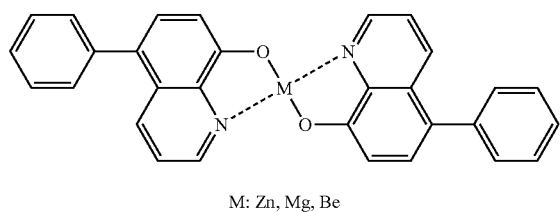
M: Zn, Mg, Be
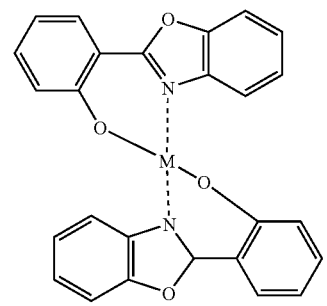
M: Zn, Mg, Be
-continued
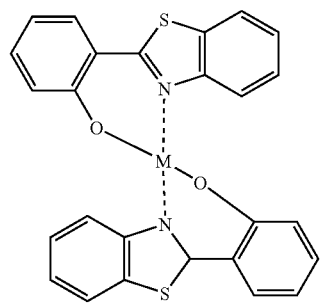
M: Zn, Mg, Be
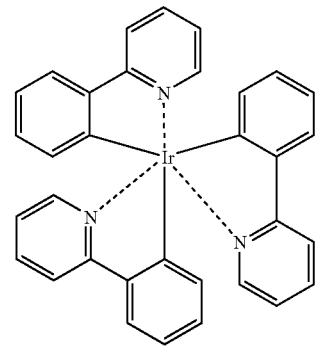
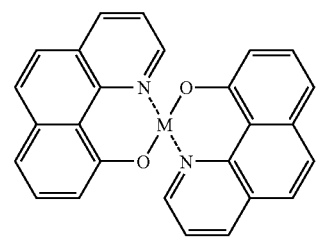
M: Zn, Mg, Be
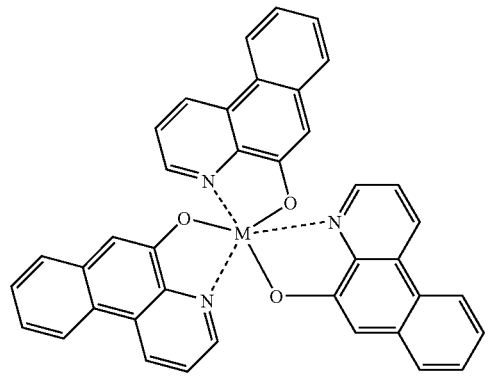
M: Al, Ga Light-Emitting Materials
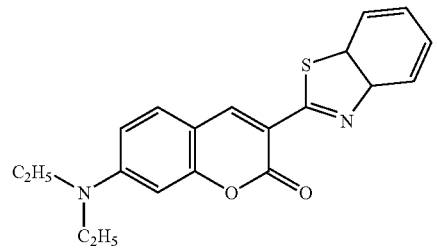
Coumarin6
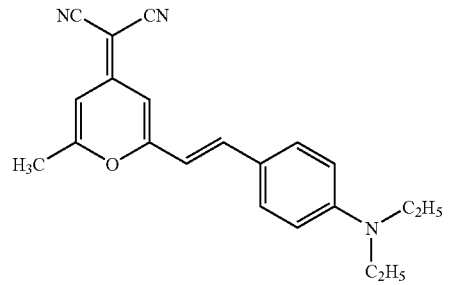
DCM-1
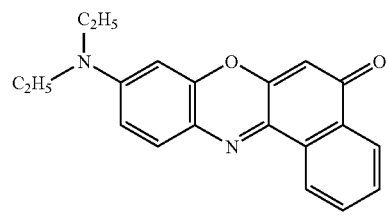
Nile red
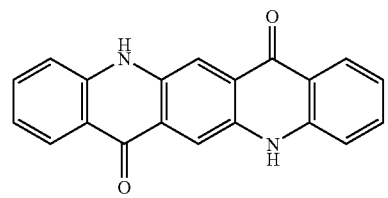
Quinacridone
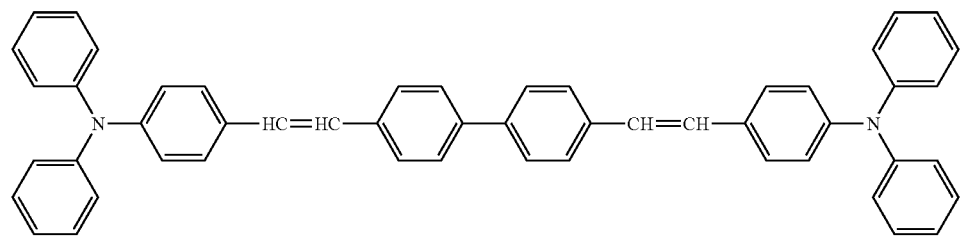
DTPABVi
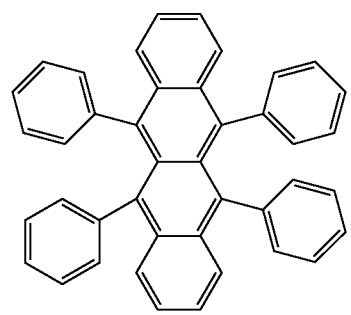
Rubrene
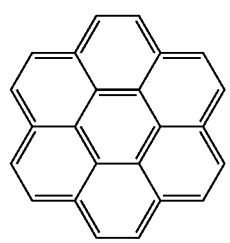
Coronene Light-Emitting Layer Matrix Materials and Electron-Transporting Materials
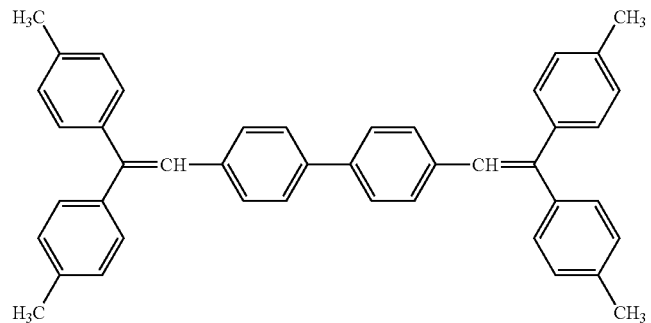
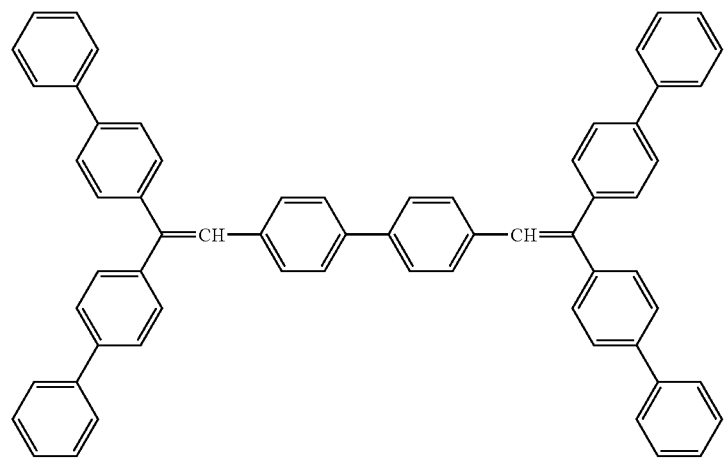
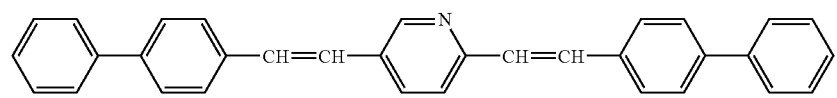
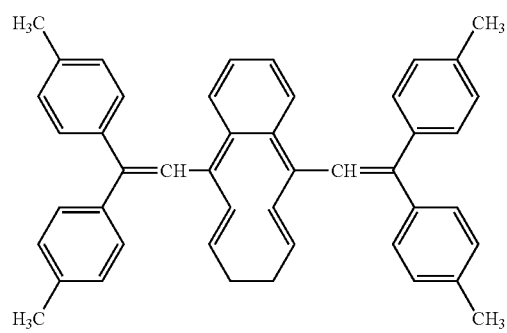
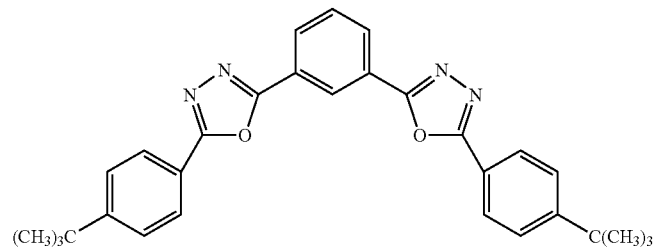

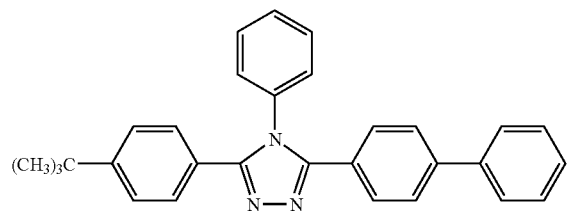
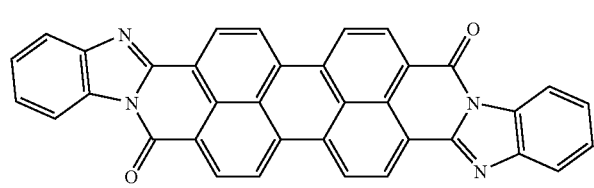
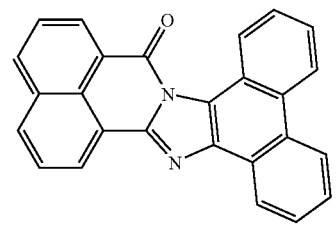
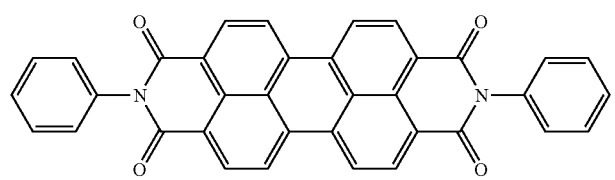
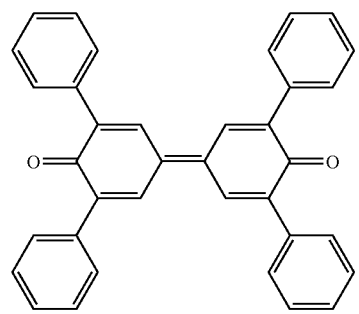
Polymer-Based Hole-Transporting Materials
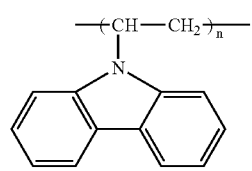
PVCz
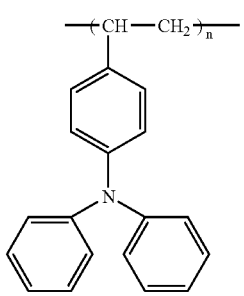
DPA-PS -continued
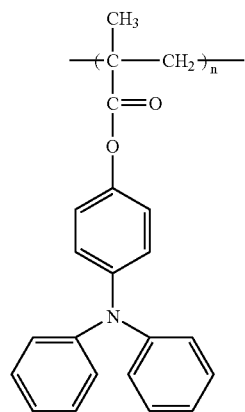
TPA-PMMA
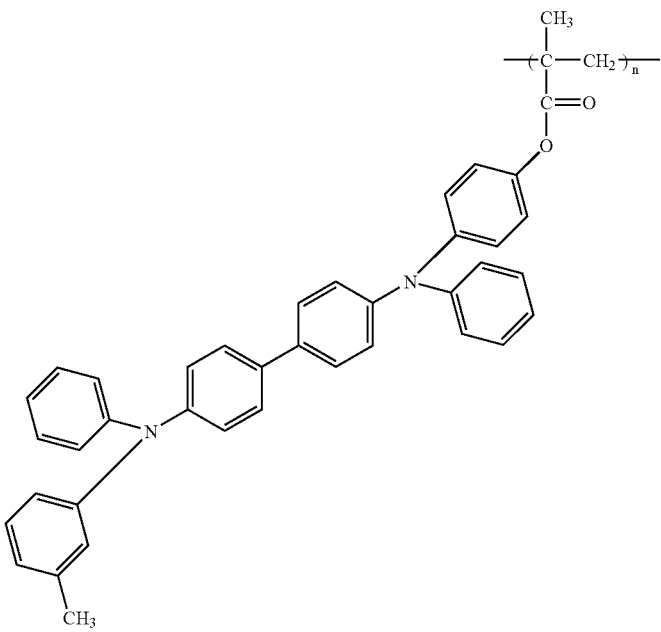
TPD-PMMA
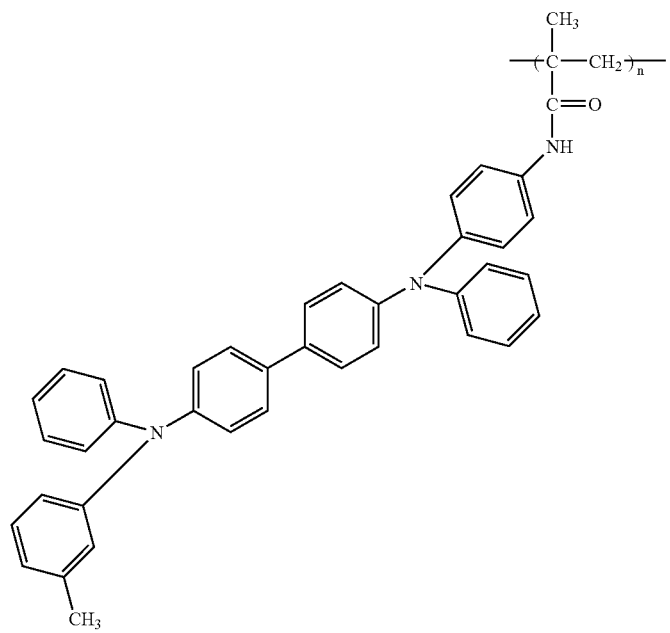
TPD-PMMA

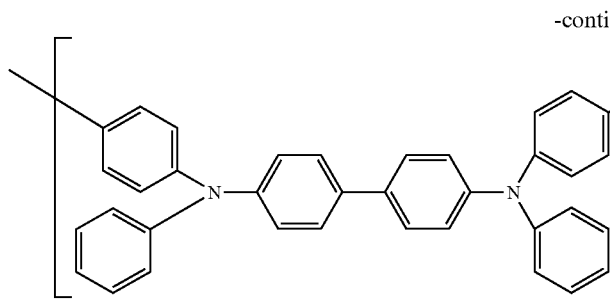
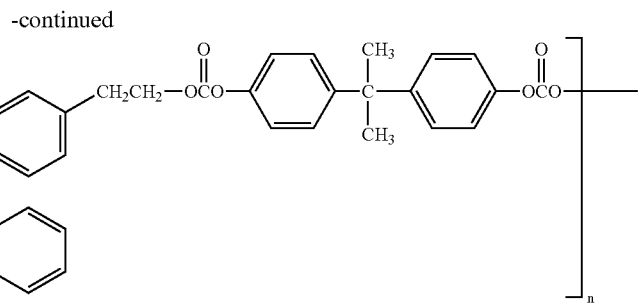

TPD-PCA

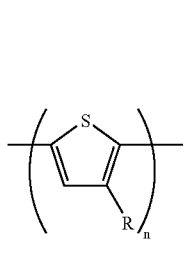

R: $C_6H_{13}$, $C_8H_{17}$, $C_{12}H_{25}$
Poly thiophene

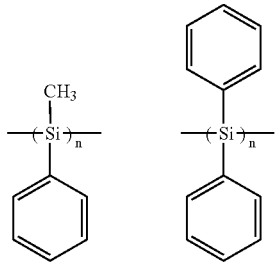

Polysilane

Polymer-Based Light-Emitting Materials and Charge-Transporting Materials

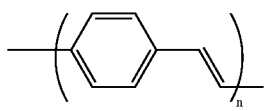

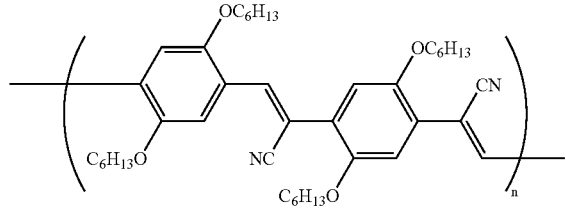

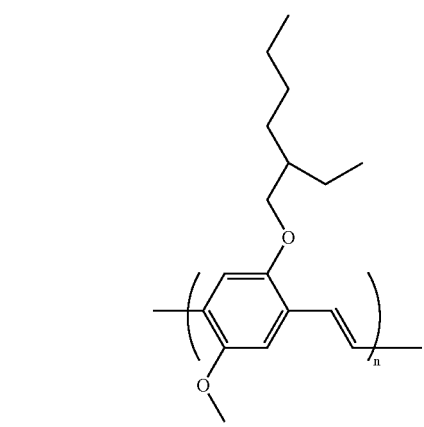

-continued

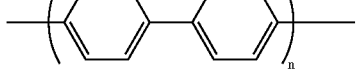

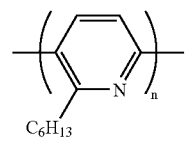

In the organic light-emitting device of the present invention, the layers containing the condensed polycyclic compounds represented by the general formula [I] or the general formula [II] and the layers containing other organic compounds are generally formed into thin films by a vacuum deposition process or a coating process in which they are dissolved in a suitable solvent. In particular, when the film is formed by a coating process, it is also possible to form the film in combination with suitable binding resins.

The above-described binding resins can be selected from a wide range of binding resins, and include, but not limited to, polyvinylcarbazole resins, polycarbonate resins, polyester resins, polyallylate resins, polystyrene resins, acrylic resins, methacrylic resins, butyral resins, polyvinylacetal resins, diallylphthalate resins, phenol resins, epoxy resins, silicone resins, polysulfone resins, urea resins and the like. In addition, one of them or a mixture of two or more of them may be used in the form of a homopolymer or a copolymer.

The materials for the anode preferably have a large work function, and elemental metals such as gold, platinum, nickel, palladium, cobalt, serene, vanadium and alloys thereof and metal oxides such as tin oxides, zinc oxides, indium tin oxides (ITO) and indium zinc oxides can be used. In addition, conductive polymers such as polyaniline, polypyrrole, polythiophene and poyphenylene sulfide can be used. These electrode materials can be used singly or in combination.

On the other hand, the materials for the cathode preferably have a small work function, and elemental metals such as lithium, sodium, potassium, calcium, magnesium, aluminum, indium, silver, lead, tin and chrome and alloys thereof can be used. Metal oxides such as indium tin oxides (ITO) can also be used. The cathode may have one-layered structure or may have a multilayered structure.

The substrates for use in the present invention include, but not limited to, metal substrates, opaque substrates such as ceramic substrates, transparent substrates such as glass, quartz and plastic sheet. Moreover, it is possible to control the color of emitted light using a color filter film, a fluorescent color conversion filter film, a dielectric reflecting film and the like for the substrate.

Furthermore, a protective layer or a sealing layer can also be provided to the prepared device for the purpose of preventing contact with oxygen, moisture and the like. The protective layer includes an inorganic material film such as a diamond thin film, a metal oxide or a metal nitride; a polymeric film such as a fluororesin, polyparaxylene, polyethylene, a silicone resin and a polystyrene resin; a photocurable resin or the like. Moreover, the device itself can be covered with glass, a gas-impermeable film, metal or the like and packaged with a suitable sealing resin.

EXAMPLES

The present invention will now be described in detail with reference to examples, but the present invention is not limited to them.

Example of Synthesis 1 (Synthesis of the Illustrated Compounds No. 1 and No. 11)

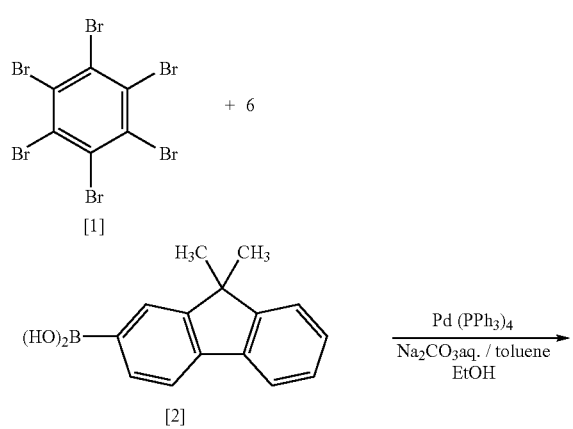

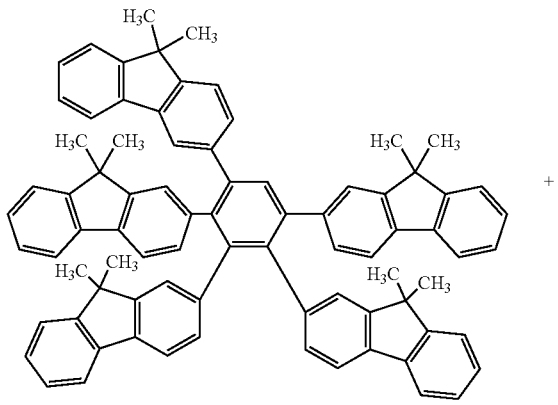

No. 1

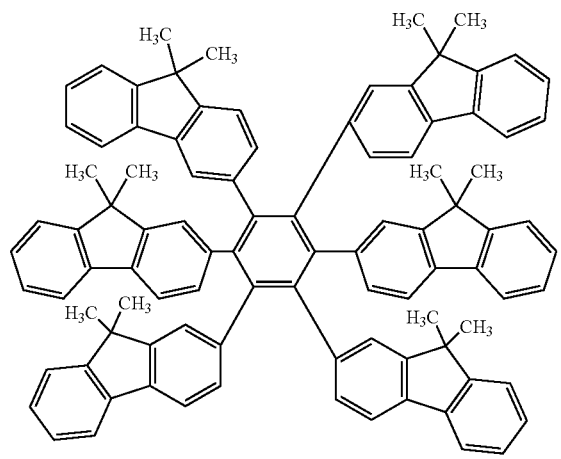

No. 11

To a three-necked flask of 500 ml, 1.4 g (2.54 mmol) of hexabromobenzene [1], 6.0 g (25.4 mmol) of 9,9-dimethylfluorene-2-boronic acid [2], 160 ml of toluene and 80 ml of ethanol were charged and an aqueous solution of 30 g of sodium carbonate/150 ml of water was dropped under stirring at room temperature in a nitrogen atmosphere, and then 0.9 g (0.78 mmol) of tetrakis(triphenylphosphine)palladium (0) was added. After stirring at room temperature for 30 minutes, the mixture was raised to a temperature of 77° C. and stirred for 20 hours. After the reaction was completed, the organic layer was extracted with chloroform, dried with anhydrous sodium sulfate and purified with a silica gel column (hexane+toluene mixed developing solvent), obtaining 0.44 g (yield of 17%) of the illustrated compound No. 1 (white crystal) and 1.3 g (yield of 42%) of No. 11 (white crystal).

Example of Synthesis 2 (Synthesis of the Illustrated Compound No. 2)

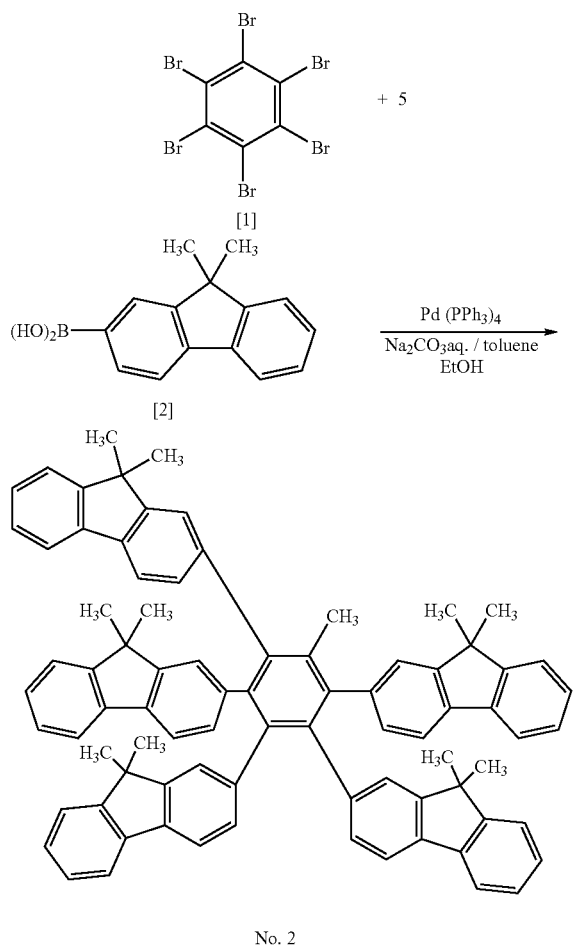

No. 2

To a three-necked flask of 300 ml, 0.5 g (1.03 mmol) of 2,3,4,5,6-pentabromotoluene [1], 2.5 g (10.3 mmol) of 9,9-dimethylfluorene-2-boronic acid [2], 100 ml of toluene and 50 ml of ethanol were charged and an aqueous solution of 10 g of sodium carbonate/50 ml of water was dropped under stirring at room temperature in a nitrogen atmosphere, and then 0.3 g (0.26 mmol) of tetrakis(triphenylphosphine)palladium (0) was added. After stirring at room temperature for 30 minutes, the mixture was raised to a temperature of 7° C. and stirred for 20 hours. After the reaction, the organic layer was extracted with chloroform before dried with anhydrous sodium sulfate and purified with a silica gel column (hexane+toluene mixed developing solvent), obtaining 0.54 g (yield of 55%) of the illustrated compound No. 2 (white crystal).

Example 1

A device having the structure shown in FIG. 2 was prepared.

On a glass substrate as the substrate 1, indium tin oxide (ITO) as the anode 2 was deposited by a sputtering process in a thickness of 120 nm and ultrasonically cleaned with acetone and isopropyl alcohol (IPA) in this order, and dried after the cleaning by boiling with IPA. Further, it was cleaned with UV/ozone. The resultant structure is referred to a transparent conductive supporting substrate.

On the transparent conductive supporting substrate, a 0.5% by weight chloroform solution of the compound represented by the following structural formula was applied by a spin-coating process to form a film having a thickness of 30 nm, forming the hole-transporting layer 5.

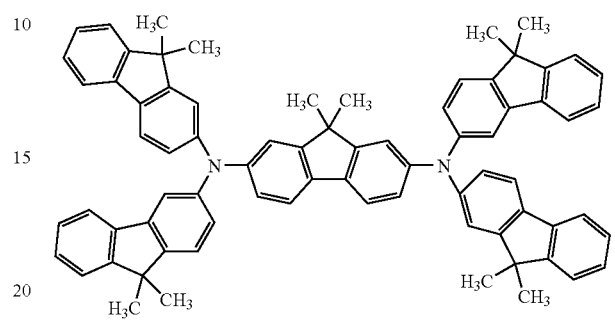

The condensed polycyclic compound represented by the illustrated compound No. 11 was deposited on the hole-transporting layer 5 by a vacuum deposition process in a thickness of 50 nm to form the electron-transporting layer 6. As for the conditions, the degree of the vacuum at the vapor deposition was $1.0 \times 10^{-4}$ Pa and the speed of deposition was 0.2 to 0.3 nm/sec.

A vapor deposition material consisting of aluminum and lithium (lithium concentration of 1 atomic %) was used to form a metal layer film having a thickness of 50 nm on the electron-transporting layer 6 by a vacuum deposition process, and further by the vacuum deposition process an aluminum layer having a thickness of 150 nm was provided to form the cathode 4. As for the conditions, the degree of the vacuum at the vapor deposition was $1.0 \times 10^{-4}$ Pa and the speed of deposition was 1.0 to 1.2 nm/sec.

The resultant structure was covered with a protective glass plate in a nitrogen atmosphere and sealed with an acrylic resin-based adhesive material.

When the thus obtained organic EL device was applied with a direct-current voltage of 10 V using an ITO electrode (anode 2) as a positive electrode and an Al—Li electrode (cathode 4) as a negative electrode, the current passed through the device at a current density of 12.0 mA/cm$^2$ and the light emission of blue color was observed at a luminance of 2,800 cd/m$^2$.

In addition, when the voltage was applied for 100 hours while maintaining the current density at 10.0 mA/cm$^2$, the initial luminance of 2,200 cd/m$^2$ dropped to 2,000 cd/m$^2$ after 100 hours, exhibiting only a small reduction of luminance.

Examples 2 to 10

Devices were prepared and evaluated in the same manner as in Example 1 except that illustrated compounds shown in Table 1 replaced the illustrated compound No. 11. The results are shown in Table 1.

Comparative Examples 1 to 5

Devices were prepared and evaluated in the same manner as in Example 1 except that the compounds represented by the structural formulas below replaced the illustrated compound No. 11. The results are shown in Table 1.

TABLE 1
Comparative compound No. 1
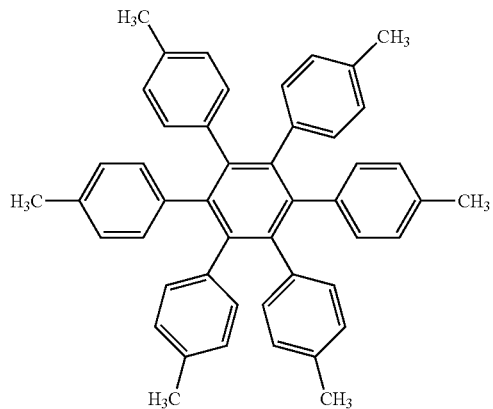
Comparative compound No. 2
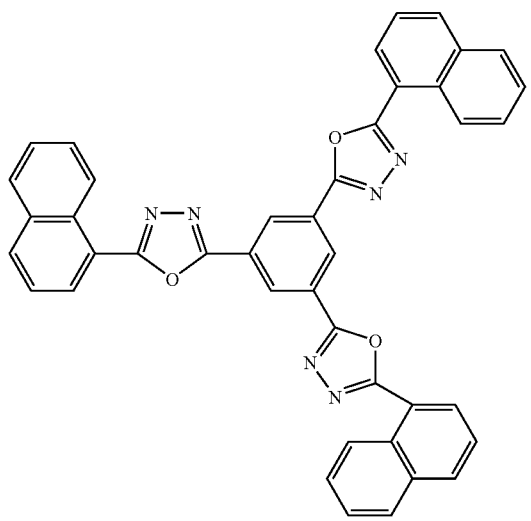
Comparative compound No. 3
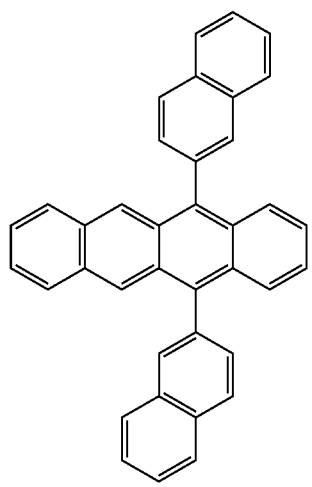

TABLE 1-continued
Comparative compound No. 4
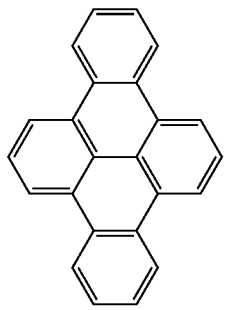
Comparative compound No. 5
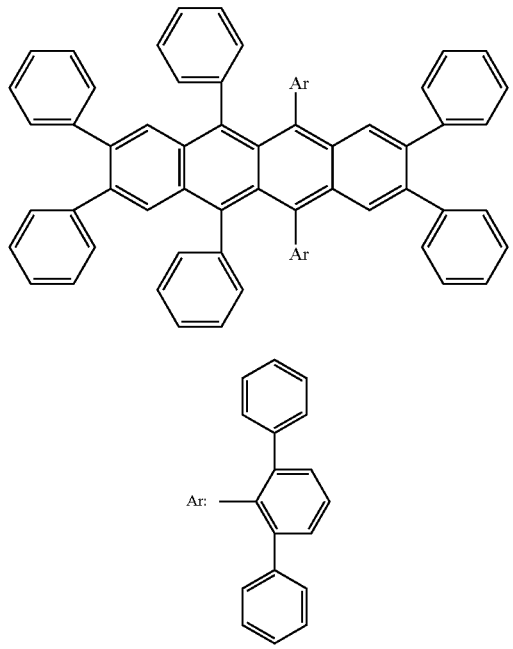
| Example No. | | Illustrated Compound No. | Initial | | Durability | | Luminance After 100 Hours (cd/m$^2$) |
|---|---|---|---|---|---|---|---|
| | | | Applied Voltage (V) | Luminance (cd/m$^2$) | Current Density (mA/cm$^2$) | Initial Luminance (cd/m$^2$) | |
| Example | 1 | 11 | 10 | 2,800 | 10.0 | 2,200 | 2,000 |
| | 2 | 1 | 10 | 2,600 | 10.0 | 1,900 | 1,600 |
| | 3 | 3 | 10 | 3,000 | 10.0 | 2,400 | 2,000 |
| | 4 | 6 | 10 | 1,900 | 10.0 | 1,400 | 1,100 |
| | 5 | 8 | 10 | 1,800 | 10.0 | 1,500 | 1,300 |
| | 6 | 9 | 10 | 2,000 | 10.0 | 1,500 | 1,200 |
| | 7 | 12 | 10 | 2,400 | 10.0 | 1,900 | 1,500 |
| | 8 | 14 | 10 | 950 | 10.0 | 800 | 700 |
| | 9 | 17 | 10 | 1,700 | 10.0 | 1,400 | 1,300 |
| | 10 | 21 | 10 | 2,200 | 10.0 | 1,900 | 1,500 |
| Comparative Example | 1 | Comparative Compound 1 | 10 | 150 | 10.0 | 140 | No Light Emission |
| | 2 | 2 | 10 | 170 | 10.0 | 150 | No Light Emission |
| | 3 | 3 | 10 | 300 | 10.0 | 250 | 30 |
| | 4 | 4 | 10 | 250 | 10.0 | 240 | 90 |
| | 5 | 5 | 10 | 450 | 10.0 | 420 | 150 |

Example 11

The device shown in FIG. 3 was prepared.

The hole-transporting layer 5 was formed on the transparent conductive supporting substrate in the same manner as in Example 1.

Comparative Examples 6 to 10

Devices were prepared and evaluated in the same manner as in Example 11 except that the comparative compounds No. 1 to 5 replaced the illustrated compound No. 1. The results are shown in Table 2.

TABLE 2

| Example No. | | Illustrated Compound No. | Initial | | Durability | | |
|---|---|---|---|---|---|---|---|
| | | | Applied Voltage (V) | Luminance (cd/m$^2$) | Current Density (mA/cm$^2$) | Initial Luminance (cd/m$^2$) | Luminance After 100 Hours (cd/m$^2$) |
| Example | 11 | 1 | 8 | 5,800 | 10.0 | 4,500 | 4,200 |
| | 12 | 2 | 8 | 5,300 | 10.0 | 4,200 | 4,000 |
| | 13 | 4 | 8 | 2,900 | 10.0 | 2,200 | 2,000 |
| | 14 | 7 | 8 | 4,200 | 10.0 | 3,400 | 3,200 |
| | 15 | 10 | 8 | 3,000 | 10.0 | 2,400 | 2,000 |
| | 16 | 13 | 8 | 3,100 | 10.0 | 2,200 | 2,000 |
| | 17 | 15 | 8 | 3,600 | 10.0 | 2,800 | 2,300 |
| | 18 | 18 | 8 | 3,700 | 10.0 | 2,700 | 2,500 |
| | 19 | 20 | 8 | 2,800 | 10.0 | 2,400 | 2,100 |
| | 20 | 22 | 8 | 3,200 | 10.0 | 2,500 | 2,200 |
| Comparative Example | 6 | Comparative Compound 1 | 8 | 350 | 10.0 | 300 | No Light Emission |
| | 7 | 2 | 8 | 400 | 10.0 | 350 | No Light Emission |
| | 8 | 3 | 8 | 1,000 | 10.0 | 850 | 100 |
| | 9 | 4 | 8 | 750 | 10.0 | 650 | 50 |
| | 10 | 5 | 8 | 1,500 | 10.0 | 1,100 | 350 |

The condensed polycyclic compound represented by the illustrated compound No. 1 was deposited on the hole-transporting layer 5 by a vacuum deposition process in a thickness of 20 nm to form the light-emitting layer 3. As for the conditions, the degree of the vacuum at the vapor deposition was $1.0 \times 10^{-4}$ Pa and the speed of deposition was 0.2 to 0.3 nm/sec.

Aluminum-trisquinolinol was deposited on the light-emitting layer 3 by a vacuum deposition process in a thickness of 40 nm to form the electron-transporting layer 6. As for the conditions, the degree of the vacuum at the vapor deposition was $1.0 \times 10^{-4}$ Pa and the speed of deposition was 0.2 to 0.3 nm/sec.

The device was sealed after the cathode 4 was formed in the same manner as in Example 1.

When the thus obtained device was applied with a direct-current voltage of 8 V using an ITO electrode (anode 2) as a positive electrode and an Al—Li electrode (cathode 4) as a negative electrode, the current having a current density of 14.0 mA/cm$^2$ passed through the device and the light emission of blue color was observed at a luminance of 5,800 cd/m$^2$.

In addition, when the voltage was applied for 100 hours while maintaining the current density at 10.0 mA/cm$^2$, the initial luminance of 4,500 cd/m$^2$ dropped to 4,200 cd/m$^2$ after 100 hours, exhibiting only a small reduction of luminance.

Examples 12 to 20

Devices were prepared and evaluated in the same manner as in Example 11 except that illustrated compounds shown in Table 2 replaced the illustrated compound No. 1. The results are shown in Table 2.

Example 21

The device shown in FIG. 3 was prepared.

On the transparent conductive supporting substrate similar to that in Example 1, a 0.5% by weight chloroform solution of the compound represented by the following structural formula was applied by a spin-coating process to form a film having a thickness of 20 nm, forming the hole-transporting layer 5.

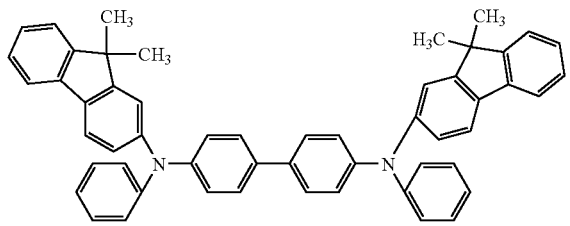

In addition, the condensed polycyclic compound represented by the illustrated compound No. 11 and the fluorene compound represented by the illustrated compound No. FL-6 (weight ratio of 100:1) were deposited by a vacuum deposition process in a thickness of 20 nm to form the light-emitting layer 3. As for the conditions, the degree of the vacuum at the vapor deposition was $1.0 \times 10^{-4}$ Pa and the speed of deposition was 0.2 to 0.3 nm/sec.

Moreover, aluminum-trisquinolinol was deposited by a vacuum deposition process in a thickness of 40 nm to form the electron-transporting layer 6. As for the conditions for deposition, the degree of the vacuum at the vapor deposition was $1.0 \times 10^{-4}$ Pa and the speed of deposition was 0.2 to 0.3 nm/sec.

The device was then sealed after the cathode 4 was formed in the same manner as in Example 1.

When the thus obtained device was applied with a direct-current voltage of 8 V using an ITO electrode (anode 2) as a positive electrode and an Al—Li electrode (cathode 4) as a negative electrode, the current passed through the device at a current density of 13.0 mA/cm$^2$ and the light emission of blue color was observed at a luminance of 13,000 cd/m$^2$.

In addition, when the voltage was applied for 100 hours while maintaining the current density at 10.0 mA/cm$^2$, the initial luminance of 10,000 cd/m$^2$ dropped to 8,900 cd/m$^2$ after 100 hours, exhibiting only a small reduction of luminance.

Examples 22 to 40

Devices were prepared and evaluated in the same manner as in Example 21 except that illustrated fluorene compounds shown in Table 3 replaced the illustrated fluorene compound No. FL-6. The results are shown in Table 3.

Comparative Examples 11 to 15

Devices were prepared and evaluated in the same manner as in Example 21 except that the comparative compounds No. 1 to 5 replaced the illustrated compound No. 11. The results are shown in Table 3.

Example 41

The device shown in FIG. 3 was prepared.

On the transparent conductive supporting substrate similar to that in Example 1, a 0.5% by weight chloroform solution of the compound represented by the following structural formula was applied by a spin-coating process to form a film having a thickness of 20 nm, forming the hole-transporting layer 5.

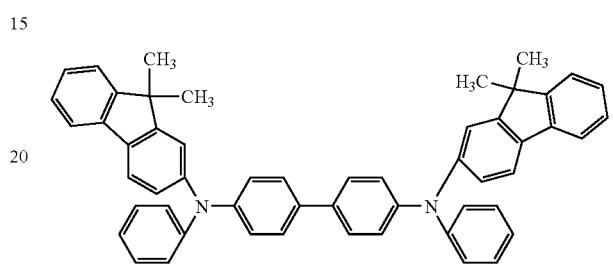

In addition, the condensed polycyclic compound represented by the illustrated compound No. 2 and the compound represented by the following structural formula (weight ratio of 100:5) were deposited by a vacuum deposition process in a thickness of 20 nm to form the light-emitting layer 3. As for the conditions for deposition, the degree of the vacuum at the vapor deposition was 1.0×10$^{-4}$ Pa and the speed of deposition was 0.2 to 0.3 nm/sec.

TABLE 3

| Example No. | | Illustrated Compound No. | Illustrated Compound No. | Initial Applied Voltage (V) | Initial Luminance (cd/m$^2$) | Current Density (mA/cm$^2$) | Durability Initial Luminance (cd/m$^2$) | Durability Luminance After 100 Hours (cd/m$^2$) |
|---|---|---|---|---|---|---|---|---|
| Example | 21 | 11 | FL-6 | 8 | 13,000 | 10.0 | 10,000 | 9,000 |
| | 22 | 11 | FL-1 | 8 | 11,000 | 10.0 | 8,500 | 8,000 |
| | 23 | 11 | FL-2 | 8 | 11,000 | 10.0 | 8,000 | 7,000 |
| | 24 | 11 | FL-3 | 8 | 8,500 | 10.0 | 7,500 | 6,500 |
| | 25 | 11 | FL-4 | 8 | 13,000 | 10.0 | 9,500 | 7,500 |
| | 26 | 11 | FL-5 | 8 | 12,000 | 10.0 | 9,000 | 7,000 |
| | 27 | 11 | FL-7 | 8 | 7,000 | 10.0 | 6,000 | 5,500 |
| | 28 | 11 | FL-8 | 8 | 7,500 | 10.0 | 6,500 | 6,000 |
| | 29 | 11 | FL-9 | 8 | 12,000 | 10.0 | 10,000 | 9,000 |
| | 30 | 11 | FL-10 | 8 | 6,500 | 10.0 | 6,000 | 5,500 |
| | 31 | 11 | FL-11 | 8 | 15,000 | 10.0 | 12,000 | 11,000 |
| | 32 | 11 | FL-12 | 8 | 9,000 | 10.0 | 8,000 | 6,500 |
| | 33 | 11 | FL-13 | 8 | 7,000 | 10.0 | 6,500 | 6,000 |
| | 34 | 11 | FL-14 | 8 | 8,000 | 10.0 | 6,500 | 5,500 |
| | 35 | 11 | FL-15 | 8 | 11,000 | 10.0 | 9,000 | 8,000 |
| | 36 | 11 | FL-16 | 8 | 16,000 | 10.0 | 13,000 | 11,000 |
| | 37 | 11 | FL-17 | 8 | 13,000 | 10.0 | 11,000 | 9,500 |
| | 38 | 11 | FL-18 | 8 | 9,500 | 10.0 | 8,000 | 6,500 |
| | 39 | 11 | FL-19 | 8 | 7,500 | 10.0 | 6,000 | 5,000 |
| | 40 | 11 | FL-20 | 8 | 6,500 | 10.0 | 6,000 | 5,000 |
| Comparative Example | 11 | Comparative Compound 1 | 1 | 8 | 2,500 | 10.0 | 2,000 | 300 |
| | 12 | Comparative Compound 2 | 2 | 8 | 2,000 | 10.0 | 15,000 | No Light Emission |
| | 13 | | 3 3 | 8 | 3,000 | 10.0 | 25,000 | 600 |
| | 14 | | 4 4 | 8 | 2,500 | 10.0 | 2,000 | 400 |
| | 15 | | 5 5 | 8 | 3,500 | 10.0 | 3,000 | 1,000 |

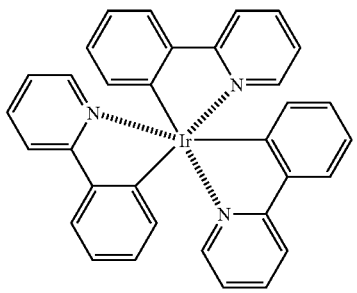

Moreover, bathophenanthroline (BPhen) was deposited by a vacuum deposition process in a thickness of 40 nm to form the electron-transporting layer 6. As for the conditions for deposition, the degree of the vacuum at the vapor deposition was $1.0 \times 10^{-4}$ Pa and the speed of deposition was 0.2 to 0.3 nm/sec.

The device was then sealed after the cathode 4 was formed in the same manner as in Example 1.

When the thus obtained device was applied with a direct-current voltage of 8 V using an ITO electrode (anode 2) as a positive electrode and an Al—Li electrode (cathode 4) as a negative electrode, the current passed through the device at a current density of 9.5 mA/cm² and the light emission of green color was observed at a luminance of 7,000 cd/m².

In addition, when the voltage was applied for 100 hours while maintaining the current density at 7.0 mA/cm², the initial luminance of 5,000 cd/m² dropped to 4,500 cd/m² after 100 hours, exhibiting only a small reduction of luminance.

Examples 42 to 50

Devices were prepared and evaluated in the same manner as in Example 41 except that illustrated compounds shown in Table 4 replaced the illustrated compound No. 2. The results are shown in Table 4.

Comparative Examples 16 to 20

Devices were prepared and evaluated in the same manner as in Example 41 except that the comparative compounds No. 1 to 5 replaced the illustrated compound No. 2. The results are shown in Table 4.

TABLE 4

| Example No. | | Illustrated Compound No. | | Initial | | Durability | | |
|---|---|---|---|---|---|---|---|---|
| | | | | Applied Voltage (V) | Luminance (cd/m²) | Current Density (mA/cm²) | Initial Luminance (cd/m²) | Luminance After 100 Hours (cd/m²) |
| Example | 41 | 2 | | 8 | 7,000 | 7.0 | 5,000 | 4,500 |
| | 42 | 3 | | 8 | 6,500 | 7.0 | 5,000 | 4,000 |
| | 43 | 5 | | 8 | 8,000 | 7.0 | 6,500 | 6,000 |
| | 44 | 6 | | 8 | 7,000 | 7.0 | 6,000 | 5,000 |
| | 45 | 13 | | 8 | 6,000 | 7.0 | 5,000 | 4,500 |
| | 46 | 15 | | 8 | 8,500 | 7.0 | 7,500 | 6,500 |
| | 47 | 16 | | 8 | 7,000 | 7.0 | 6,500 | 6,000 |
| | 48 | 19 | | 8 | 4,500 | 7.0 | 4,000 | 3,500 |
| | 49 | 20 | | 8 | 5,000 | 7.0 | 4,000 | 3,000 |
| | 50 | 22 | | 8 | 6,500 | 7.0 | 5,500 | 4,500 |
| Comparative | 16 | Comparative | 1 | 8 | 900 | 7.0 | 800 | 100 |
| Example | 17 | Compound | 2 | 8 | 650 | 7.0 | 600 | No Light Emission |
| | 18 | | 3 | 8 | 1,500 | 7.0 | 1,000 | 300 |
| | 19 | | 4 | 8 | 1,000 | 7.0 | 850 | 100 |
| | 20 | | 5 | 8 | 2,000 | 7.0 | 1,500 | 550 |

Example 51

The device shown in FIG. 1 was prepared.

On the transparent conductive supporting substrate similar to that in Example 1, a solution in which 0.050 g of the condensed polycyclic compound represented by the illustrated compound No. 1 and 1.00 g of poly-N-vinylcarbazole (weight average molecular weight=63,000) were dissolved in 80 ml of chloroform was applied by a spin-coating process (the number of revolutions=2,000 rpm) to form a film having a thickness of 120 nm, forming the organic layer (light-emitting layer 3).

The device was then sealed after the cathode 4 was formed in the same manner as in Example 1.

When the thus obtained device was applied with a direct-current voltage of 10 V using an ITO electrode (anode 2) as a positive electrode and an Al—Li electrode (cathode 4) as a negative electrode, the current passed through the device at a current density of 7.7 mA/cm$^2$ and the light emission of blue color was observed at a luminance of 1,400 cd/m$^2$.

In addition, when the voltage was applied for 100 hours while maintaining the current density at 5.0 mA/cm$^2$ in a nitrogen atmosphere, the initial luminance of 950 cd/m$^2$ dropped to 900 cd/m$^2$ after 100 hours, exhibiting only a small reduction of luminance.

Examples 52 to 55

Devices were prepared and evaluated in the same manner as in Example 51 except that illustrated compounds shown in Table 5 replaced the illustrated compound No. 1. The results are shown in Table 5.

Comparative Examples 21 to 25

Devices were prepared and evaluated in the same manner as in Example 51 except that the comparative compounds No. 1 to 5 replaced the illustrated compound No. 1. The results are shown in Table 5.

As described above by illustrating embodiments and examples, the organic light-emitting devices using the condensed polycyclic compounds represented by the general formula [I] or the general formula [II] provide the light-emission having high luminance at a low applied voltage and are also excellent in durability. Particularly, the organic layers containing the condensed polycyclic compounds of the present invention are excellent as an electron-transporting layer as well as a light-emitting layer.

Moreover, it is possible to prepare the devices by using a vacuum deposition process, casting process or the like, and the devices having a large area can be prepared easily at a relatively low cost.

The invention claimed is:

1. A condensed polycyclic compound represented by the following structural formula:

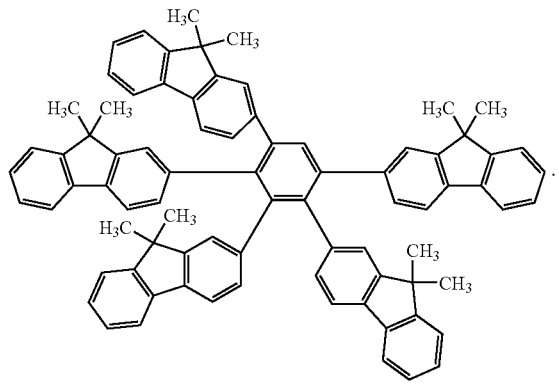

2. A condensed polycyclic compound represented by the following structural formula:

TABLE 5

| Example No. | | Illustrated Compound No. | | Initial | | Durability | | |
|---|---|---|---|---|---|---|---|---|
| | | | Applied Voltage (V) | Luminance (cd/m$^2$) | Current Density (mA/cm$^2$) | Initial Luminance (cd/m$^2$) | Luminance After 100 Hours (cd/m$^2$) |
| Example | 51 | 1 | | 10 | 1,400 | 5.0 | 950 | 900 |
| | 52 | 2 | | 10 | 1,200 | 5.0 | 900 | 800 |
| | 53 | 11 | | 10 | 1,500 | 5.0 | 1,200 | 1,100 |
| | 54 | 17 | | 10 | 1,400 | 5.0 | 1,000 | 950 |
| | 55 | 19 | | 10 | 1,300 | 5.0 | 1,000 | 850 |
| Comparative Example | 16 | Comparative Compound | 1 | 10 | 250 | 5.0 | 200 | No Light Emission |
| | 17 | | 2 | 10 | 150 | 5.0 | 100 | No Light Emission |
| | 18 | | 3 | 10 | 350 | 5.0 | 300 | No Light Emission |
| | 19 | | 4 | 10 | 300 | 5.0 | 250 | No Light Emission |
| | 20 | | 5 | 10 | 550 | 5.0 | 450 | 100 |

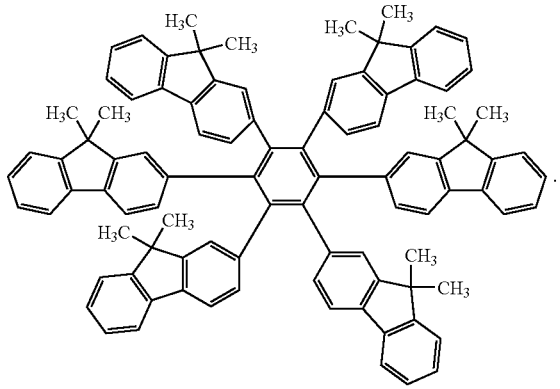

3. An organic light-emitting device comprising a pair of electrodes consisting of an anode and a cathode and one or a plurality of organic compound-containing layers sandwiched between the pair of electrodes, wherein at least one layer of the organic compound-containing layers contains at least the condensed polycyclic compound according to claim 1.

4. An organic light-emitting device comprising a pair of electrodes consisting of an anode and a cathode and one or a plurality of organic compound-containing layers sandwiched between the pair of electrodes, wherein at least one layer of the organic compound-containing layers contains at least the condensed polycyclic compound according to claim 2.

5. The organic light-emitting device according to claim 3, wherein at least one layer of the organic compound-containing layers containing the condensed polycyclic compound is an electron-transporting layer or a light-emitting layer.

6. The organic light-emitting device according to claim 4, wherein at least one layer of the organic compound-containing layers containing the condensed polycyclic compound is an electron-transporting layer or a light-emitting layer.

7. The organic light-emitting device according to claim 3, wherein at least one of the layers containing the condensed polycyclic compound is a light-emitting layer containing a fluorene compound represented by general formula [VIII]:

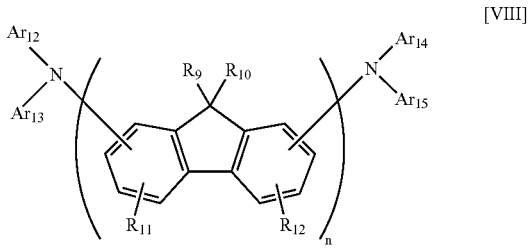

wherein $R_9$ and $R_{10}$ are the same or different and are each independently hydrogen or a group selected from the group consisting of alkyl, aralkyl, aryl and heterocyclic, each having no substituent or a substituent; any pair of $R_9$ combined to their respective fluorene structures are the same or different to each other; any pair of $R_{10}$ combined to their respective fluorene structures are the same or different to each other; $R_{11}$ and $R_{12}$ are the same or different and are each independently hydrogen, halogen, cyano or a group selected from the group consisting of alkyl, aralkyl, aryl and heterocyclic, each having no substituent or a substituent; any pair of $R_{11}$ combined to their respective fluorene structures are the same or different to each other; any pair of $R_{12}$ combined to their respective fluorene structures are the same or different to each other; $Ar_{12}$, $Ar_{13}$, $Ar_{14}$ and $Ar_{15}$ are the same or different and are each independently a group selected from the group consisting of aromatic, heterocyclic, condensed polycyclic aromatic and condensed polycyclic heterocyclic, each having no substituent or a substituent, and $Ar_{12}$ and $Ar_{14}$ can be bonded to $Ar_{13}$ and $Ar_{15}$ respectively to form a ring; and n is an integer from 1 to 10.

8. The organic light-emitting device according to claim 4, wherein at least one of the layers containing the condensed polycyclic compound is a light-emitting layer containing a fluorene compound represented by general formula [VIII]:

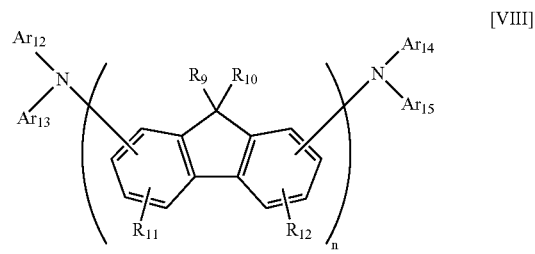

wherein $R_9$ and $R_{10}$ are the same or different and are each independently hydrogen, halogen, cyano or a group selected from the group consisting of alkyl, aralkyl, aryl and heterocyclic, each having no substituent or a substituent; any pair of $R_9$ combined to their respective fluorene structures are the same or different to each other; any pair of $R_{10}$ combined to their respective fluorene structures are the same or different to each other; $R_{11}$ and $R_{12}$ are the same or diffenrent and are each independently hydrogen, halogen, cyano or a group selected from the group consisting of alkyl, aralkyl, aryl and heterocyclic, each having no substituent or a substituent; any pair of $R_{11}$ combined to their respective fluorene structures are the same or different to each other; any pair of $R_{12}$ combined to their respective fluorene structures are the same or different to each other; $Ar_{12}$, $Ar_{13}$, $Ar_{14}$ and $Ar_{15}$ are the same or different and are each independently a group selected from the group consisting of aromatic, heterocyclic, condensed polycyclic aromatic and condensed polycyclic heterocyclic, each having no substituent or a substituent, and $Ar_{12}$ and $Ar_{14}$ can be bonded to $Ar_{13}$ and $Ar_{15}$ respectively to form a ring; and n is an integer from 1 to 10.

9. The organic light-emitting device according to claim 3, wherein at least one of the layers containing the condensed polycyclic compound is a light-emitting layer containing a fluorene compound represented by general formula [IX]:

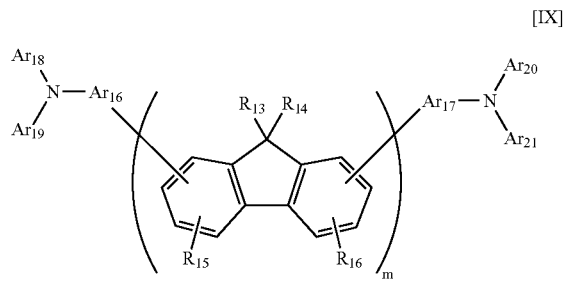

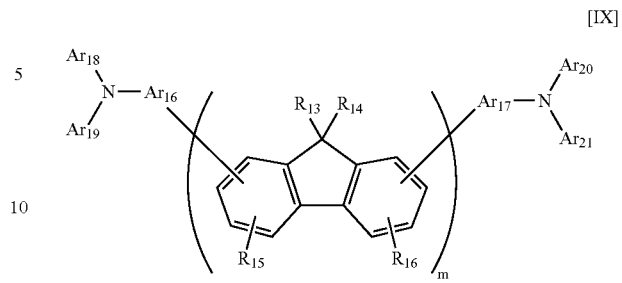

wherein $R_{13}$ and $R_{14}$ are the same or different and are each independently hydrogen or a group selected from the group consisting of alkyl, aralkyl, aryl and heterocyclic, each having no substituent or a substituent; any pair of $R_{13}$ combined to their respective fluorene structures are the same or different to each other; any pair of $R_{14}$ combined to their respective fluorene structures are the same or different to each other; $R_{15}$ and $R_{16}$ are the same or different and are each independently hydrogen, halogen, cyano or a group selected from the group consisting of alkyl, aralkyl, aryl and heterocyclic, each having no substituent or a substituent; any pair of $R_{15}$ combined to their respective fluorene structures are the same or different to each other; any pair of $R_{16}$ combined to their respective fluorene structures are the same or different to each other; $Ar_{16}$ and $Ar_{17}$ are the same or different and are each independently a divalent group selected from the group consisting of divalent aromatic and divalent heterocyclic, each having no substituent or a substituent; $Ar_{18}$, $Ar_{19}$, $Ar_{20}$ and $Ar_{21}$ are the same or different and are each independently a group selected from the group consisting of aromatic, heterocyclic, condensed polycyclic aromatic and condensed polycyclic heterocyclic, each having no substituent or a substituent, and $Ar_{18}$ and $Ar_{20}$ can be bonded to $Ar_{19}$ and $Ar_{21}$ respectively to form a ring; and m is an integer from 1 to 10.

10. The organic light-emitting device according to claim 4, wherein at least one of the layers containing the condensed polycyclic compound is a light-emitting layer containing a fluorene compound represented by general formula [IX]:

wherein $R_{13}$ and $R_{14}$ are the same or different and are each independently hydrogen or a group selected from the group consisting of alkyl, aralkyl, aryl and heterocyclic, each having no substituent or a substituent; any pair of $R_{13}$ combined to their respective fluorene structures are the same or different to each other; any pair of $R_{14}$ combined to their respective fluorene structures are the same or different to each other; $R_{15}$ and $R_{16}$ are the same or different and are each independently hydrogen, halogen, cyano or a group selected from the group consisting of alkyl, aralkyl, aryl and heterocyclic, each having no substituent or a substituent; any pair of $R_{15}$ combined to their respective fluorene structures are the same or different to each other; any pair of $R_{16}$ combined to their respective fluorene structures are the same or different to each other; $Ar_{16}$ and $Ar_{17}$ are the same or different and are each independently a divalent group selected from the group consisting of divalent aromatic and divalent heterocyclic, each having no substituent or a substituent; $Ar_{18}$, $Ar_{19}$, $Ar_{20}$ and $Ar_{21}$ are the same or different and are each independently a group selected from the group consisting of aromatic, heterocyclic, condensed polycyclic aromatic and condensed polycyclic heterocyclic, each having no substituent or a substituent, and $Ar_{18}$ and $Ar_{20}$ can be bonded to $Ar_{19}$ and $Ar_{21}$ respectively to form a ring; and m is an integer from 1 to 10.

* * * * *